(12) United States Patent
Waldhauser et al.

(10) Patent No.: US 10,493,278 B2
(45) Date of Patent: Dec. 3, 2019

(54) CARDIAC MODULATION FACILITATION METHODS AND SYSTEMS

(71) Applicant: Cardionomic, Inc., New Brighton, MN (US)

(72) Inventors: Steven L. Waldhauser, Savage, MN (US); Steven D. Goedeke, Forest Lake, MN (US)

(73) Assignee: Cardionomic, Inc., New Brighton, MN (US)

( * ) Notice: Subject to any disclaimer, the term of this patent is extended or adjusted under 35 U.S.C. 154(b) by 0 days.

(21) Appl. No.: 15/540,161

(22) PCT Filed: Jan. 4, 2016

(86) PCT No.: PCT/US2016/012082
§ 371 (c)(1),
(2) Date: Jun. 27, 2017

(87) PCT Pub. No.: WO2016/111940
PCT Pub. Date: Jul. 14, 2016

(65) Prior Publication Data
US 2018/0050206 A1    Feb. 22, 2018

Related U.S. Application Data

(60) Provisional application No. 62/099,834, filed on Jan. 5, 2015.

(51) Int. Cl.
*A61N 1/36* (2006.01)
*A61N 1/05* (2006.01)
(Continued)

(52) U.S. Cl.
CPC .......... *A61N 1/36114* (2013.01); *A61N 1/025* (2013.01); *A61N 1/05* (2013.01);
(Continued)

(58) Field of Classification Search
CPC .............. A61N 1/36114; A61N 1/3606; A61N 1/36135; A61N 1/36146; A61N 1/08;
(Continued)

(56) References Cited

U.S. PATENT DOCUMENTS

| 4,718,423 A | 1/1988 | Willis et al. |
|---|---|---|
| 4,947,866 A | 8/1990 | Lessar et al. |

(Continued)

FOREIGN PATENT DOCUMENTS

| CA | 2 848 781 | 3/2013 |
|---|---|---|
| EP | 1 871 469 | 10/2013 |

(Continued)

OTHER PUBLICATIONS

Ardell et al., "Differential sympathetic regulation of automatic, conductile, and contractile tissue in dog heart," American Journal of Physiology (Nov. 1988) 255 (5): H1050-H1059.

(Continued)

*Primary Examiner* — Deborah L Malamud
(74) *Attorney, Agent, or Firm* — Knobbe Martens Olson & Bear, LLP

(57) ABSTRACT

A method of facilitating therapeutic neuromodulation of a heart of a patient includes positioning an electrode in a pulmonary artery, positioning a sensor in vasculature, delivering via a stimulation system first and second electrical signals of a series of electrical signals to the electrode. The second electrical signal differs from the first electrical signal by a magnitude of a first parameter of a plurality of parameters. The method includes determining, via the sensor, sensor data indicative of one or more heart activity properties in response to the delivery of the series of electrical signals, and delivering a therapeutic neuromodulation signal to the pulmonary artery using selected electrical parameters. The selected electrical parameters include a selected mag- (Continued)

nitude of the first parameter. The selected magnitude of the first parameter is based at least partially on the sensor data. The therapeutic neuromodulation signal increases heart contractility.

25 Claims, 10 Drawing Sheets

(51) Int. Cl.
*A61N 1/02* (2006.01)
*A61B 5/0402* (2006.01)
*A61B 5/00* (2006.01)
*A61B 5/01* (2006.01)
*A61B 5/145* (2006.01)
*A61B 5/0215* (2006.01)
*A61B 5/0408* (2006.01)
*A61B 7/02* (2006.01)

(52) U.S. Cl.
CPC .......... *A61N 1/056* (2013.01); *A61N 1/36139* (2013.01); *A61B 5/01* (2013.01); *A61B 5/0215* (2013.01); *A61B 5/0402* (2013.01); *A61B 5/0408* (2013.01); *A61B 5/14503* (2013.01); *A61B 5/14532* (2013.01); *A61B 5/14542* (2013.01); *A61B 5/6869* (2013.01); *A61B 7/023* (2013.01); *A61B 2560/0223* (2013.01); *A61B 2562/0219* (2013.01)

(58) Field of Classification Search
CPC ... A61N 1/04; A61N 1/18; A61N 1/37; A61B 5/4836; A61B 5/4848; A61B 5/021; A61B 5/6852; A61B 5/04001; A61B 5/486; A61B 5/02; A61B 5/024
See application file for complete search history.

(56) References Cited

U.S. PATENT DOCUMENTS

| | | |
|---|---|---|
| 4,950,227 A | 8/1990 | Savin et al. |
| 5,067,957 A | 11/1991 | Jervis |
| 5,156,154 A | 10/1992 | Valenta, Jr. et al. |
| 5,190,546 A | 3/1993 | Jervis |
| 5,197,978 A | 3/1993 | Hess |
| 5,213,098 A | 5/1993 | Bennett et al. |
| 5,224,491 A | 7/1993 | Mehra |
| 5,259,387 A | 11/1993 | Depinto |
| 5,336,244 A | 8/1994 | Weijand |
| 5,345,936 A | 9/1994 | Pomeranz et al. |
| 5,365,926 A | 11/1994 | Desai |
| 5,383,852 A | 1/1995 | Stevens-Wright et al. |
| 5,423,881 A | 6/1995 | Breyen et al. |
| 5,431,649 A | 7/1995 | Mulier et al. |
| 5,462,527 A | 10/1995 | Stevens-Wright et al. |
| 5,554,139 A | 9/1996 | Okajima |
| 5,564,434 A | 10/1996 | Halperin et al. |
| 5,598,848 A | 2/1997 | Swanson et al. |
| 5,611,777 A | 3/1997 | Bowden et al. |
| 5,711,316 A | 1/1998 | Elsberry et al. |
| 5,725,570 A | 3/1998 | Heath |
| 5,755,766 A | 5/1998 | Chastain et al. |
| 5,782,239 A | 7/1998 | Webster |
| 5,853,411 A | 12/1998 | Whayne et al. |
| 5,948,007 A | 9/1999 | Starkebaum et al. |
| 5,954,761 A | 9/1999 | Machek et al. |
| 5,968,040 A | 10/1999 | Swanson et al. |
| 5,997,563 A | 12/1999 | Kretzers |
| 6,036,697 A | 3/2000 | Dicaprio |
| 6,038,480 A | 3/2000 | Hrdlicka et al. |
| 6,058,331 A | 5/2000 | King et al. |
| 6,059,810 A | 5/2000 | Brown et al. |
| 6,071,308 A | 6/2000 | Ballou et al. |
| 6,136,021 A | 10/2000 | Tockman et al. |
| 6,152,882 A | 11/2000 | Prutchi |
| 6,161,029 A | 12/2000 | Spreigl et al. |
| 6,223,072 B1 | 4/2001 | Mika et al. |
| 6,231,516 B1 | 5/2001 | Keilman et al. |
| 6,233,484 B1 | 5/2001 | Ben-haim et al. |
| 6,233,487 B1 | 5/2001 | Mika et al. |
| 6,236,887 B1 | 5/2001 | Ben-haim et al. |
| 6,241,724 B1 | 6/2001 | Fleischman et al. |
| 6,254,610 B1 | 7/2001 | Darvish et al. |
| 6,263,242 B1 | 7/2001 | Mika et al. |
| 6,266,564 B1 | 7/2001 | Hill et al. |
| 6,285,906 B1 | 9/2001 | Ben-haim et al. |
| 6,292,693 B1 | 9/2001 | Darvish et al. |
| 6,292,695 B1 | 9/2001 | Webster et al. |
| 6,292,704 B1 | 9/2001 | Malonek et al. |
| 6,295,475 B1 | 9/2001 | Morgan |
| 6,298,268 B1 | 10/2001 | Ben-haim et al. |
| 6,304,777 B1 | 10/2001 | Ben-haim et al. |
| 6,317,631 B1 | 11/2001 | Ben-haim et al. |
| 6,319,241 B1 | 11/2001 | King et al. |
| 6,330,476 B1 | 12/2001 | Ben-haim et al. |
| 6,335,538 B1 | 1/2002 | Prutchi et al. |
| 6,348,045 B1 | 2/2002 | Malonek et al. |
| 6,353,762 B1 | 3/2002 | Baudino et al. |
| 6,360,123 B1 | 3/2002 | Kimchi et al. |
| 6,360,126 B1 | 3/2002 | Mika et al. |
| 6,363,279 B1 | 3/2002 | Ben-haim et al. |
| 6,370,430 B1 | 4/2002 | Mika et al. |
| 6,415,178 B1 | 7/2002 | Ben-haim et al. |
| 6,424,866 B2 | 7/2002 | Mika et al. |
| 6,428,537 B1 | 8/2002 | Swanson et al. |
| 6,442,424 B1 | 8/2002 | Ben-haim et al. |
| 6,447,478 B1 | 9/2002 | Maynard |
| 6,459,928 B2 | 10/2002 | Mika et al. |
| 6,463,324 B1 | 10/2002 | Ben-haim et al. |
| 6,473,653 B1 | 10/2002 | Schallhorn et al. |
| 6,480,737 B1 | 11/2002 | Policker et al. |
| 6,522,904 B1 | 2/2003 | Mika et al. |
| 6,522,926 B1 | 2/2003 | Kieval et al. |
| 6,529,778 B2 | 3/2003 | Prutchi |
| 6,542,774 B2 | 4/2003 | Hill et al. |
| 6,547,788 B1 | 4/2003 | Maguire et al. |
| 6,564,096 B2 | 5/2003 | Mest |
| 6,571,127 B1 | 5/2003 | Ben-haim et al. |
| 6,574,492 B1 | 6/2003 | Shlomo et al. |
| 6,587,721 B1 | 7/2003 | Prutchi et al. |
| 6,597,952 B1 | 7/2003 | Mika et al. |
| 6,600,953 B2 | 7/2003 | Flesler et al. |
| 6,662,055 B1 | 12/2003 | Prutchi |
| 6,669,693 B2 | 12/2003 | Friedman |
| 6,675,043 B1 | 1/2004 | Prutchi et al. |
| 6,684,105 B2 | 1/2004 | Cohen et al. |
| 6,694,192 B2 | 2/2004 | Policker et al. |
| 6,712,831 B1 | 3/2004 | Kaplan et al. |
| 6,725,093 B1 | 4/2004 | Ben-haim et al. |
| 6,738,655 B1 | 5/2004 | Sen et al. |
| 6,740,113 B2 | 5/2004 | Vrba |
| 6,748,271 B2 | 6/2004 | Spinelli et al. |
| 6,749,600 B1 | 6/2004 | Levy |
| 6,754,532 B1 | 6/2004 | Ferek-Petric |
| RE38,654 E | 11/2004 | Hill et al. |
| 6,832,478 B2 | 12/2004 | Anderson et al. |
| 6,850,801 B2 | 2/2005 | Kieval et al. |
| 6,887,266 B2 | 5/2005 | Williams et al. |
| 6,912,419 B2 | 6/2005 | Hill et al. |
| 6,932,930 B2 | 8/2005 | Desimone et al. |
| 6,944,490 B1 | 9/2005 | Chow |
| 6,947,792 B2 | 9/2005 | Ben-haim et al. |
| 6,950,689 B1 | 9/2005 | Willis et al. |
| 6,985,774 B2 | 1/2006 | Kieval et al. |
| 6,993,385 B1 | 1/2006 | Routh et al. |
| 7,027,863 B1 | 4/2006 | Prutchi et al. |
| 7,062,318 B2 | 6/2006 | Ben-haim et al. |
| 7,072,720 B2 | 7/2006 | Puskas |
| 7,082,336 B2 | 7/2006 | Ransbury et al. |
| 7,092,753 B2 | 8/2006 | Darvish et al. |
| 7,092,759 B2 | 8/2006 | Nehls et al. |
| 7,096,070 B1 | 8/2006 | Jenkins et al. |
| 7,097,665 B2 | 8/2006 | Stack et al. |

(56) References Cited

U.S. PATENT DOCUMENTS

| | | |
|---|---|---|
| 7,111,627 B2 | 9/2006 | Stack et al. |
| 7,121,283 B2 | 10/2006 | Stack et al. |
| 7,141,061 B2 | 11/2006 | Williams et al. |
| 7,146,984 B2 | 12/2006 | Stack et al. |
| 7,152,607 B2 | 12/2006 | Stack et al. |
| 7,158,832 B2 | 1/2007 | Kieval et al. |
| 7,163,554 B2 | 1/2007 | Williams et al. |
| 7,167,748 B2 | 1/2007 | Ben-haim et al. |
| 7,171,263 B2 | 1/2007 | Darvish et al. |
| 7,187,970 B2 | 3/2007 | Shemer et al. |
| 7,190,997 B1 | 3/2007 | Darvish et al. |
| 7,195,594 B2 | 3/2007 | Eigler et al. |
| 7,195,637 B2 | 3/2007 | Mika |
| 7,218,963 B2 | 5/2007 | Ben-haim et al. |
| 7,231,260 B2 | 6/2007 | Wallace et al. |
| 7,260,431 B2 | 8/2007 | Libbus et al. |
| 7,277,757 B2 | 10/2007 | Casavant et al. |
| 7,277,761 B2 | 10/2007 | Shelchuk |
| 7,279,007 B2 | 10/2007 | Nikolic |
| 7,285,287 B2 | 10/2007 | Williams et al. |
| 7,295,881 B2 | 11/2007 | Cohen et al. |
| 7,308,303 B2 | 12/2007 | Whitehurst et al. |
| 7,310,555 B2 | 12/2007 | Ben-haim et al. |
| 7,321,793 B2 | 1/2008 | Ben Ezra et al. |
| 7,354,454 B2 | 4/2008 | Stack et al. |
| 7,363,082 B2 | 4/2008 | Ransbury et al. |
| 7,377,939 B2 | 5/2008 | Williams et al. |
| 7,389,149 B2 | 6/2008 | Rossing et al. |
| 7,412,289 B2 | 8/2008 | Malonek et al. |
| 7,431,725 B2 | 10/2008 | Stack et al. |
| 7,460,906 B2 | 12/2008 | Libbus |
| 7,460,907 B1 | 12/2008 | Darvish et al. |
| 7,486,991 B2 | 2/2009 | Libbus et al. |
| 7,499,742 B2 | 3/2009 | Bolea et al. |
| 7,509,166 B2 | 3/2009 | Libbus |
| 7,529,589 B2 | 5/2009 | Williams et al. |
| 7,542,800 B2 | 6/2009 | Libbus et al. |
| 7,547,286 B2 | 6/2009 | Choate |
| 7,561,923 B2 | 7/2009 | Libbus et al. |
| 7,616,997 B2 | 11/2009 | Kieval et al. |
| 7,617,003 B2 | 11/2009 | Caparso et al. |
| 7,617,007 B2 | 11/2009 | Williams et al. |
| 7,623,926 B2 | 11/2009 | Rossing et al. |
| 7,630,760 B2 | 12/2009 | Libbus et al. |
| 7,634,317 B2 | 12/2009 | Ben-David et al. |
| 7,643,875 B2 | 1/2010 | Heil, Jr. et al. |
| 7,647,102 B2 | 1/2010 | Routh et al. |
| 7,658,709 B2 | 2/2010 | Anderson et al. |
| 7,668,602 B2 | 2/2010 | Ben-David et al. |
| 7,676,266 B1 | 3/2010 | Kroll |
| 7,704,276 B2 | 4/2010 | Williams et al. |
| 7,706,884 B2 | 4/2010 | Libbus |
| 7,734,343 B2 | 6/2010 | Ransbury et al. |
| 7,734,348 B2 | 6/2010 | Zhang et al. |
| 7,747,335 B2 | 6/2010 | Williams |
| 7,765,000 B2 | 7/2010 | Zhang et al. |
| 7,769,446 B2 | 8/2010 | Moffitt et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,801,614 B2 | 9/2010 | Rossing et al. |
| 7,805,194 B1 | 9/2010 | Schecter |
| 7,805,203 B2 | 9/2010 | Ben-David et al. |
| 7,813,812 B2 | 10/2010 | Kieval et al. |
| 7,840,262 B2 | 11/2010 | Mika et al. |
| 7,840,271 B2 | 11/2010 | Kieval et al. |
| 7,840,282 B2 | 11/2010 | Williams et al. |
| 7,848,812 B2 | 12/2010 | Crowley et al. |
| 7,857,748 B2 | 12/2010 | Williams et al. |
| 7,869,881 B2 | 1/2011 | Libbus et al. |
| 7,873,413 B2 | 1/2011 | McCabe et al. |
| 7,881,782 B2 | 2/2011 | Libbus et al. |
| 7,885,709 B2 | 2/2011 | Ben-David |
| 7,885,711 B2 | 2/2011 | Ben-Ezra et al. |
| 7,890,185 B2 | 2/2011 | Cohen et al. |
| 7,892,292 B2 | 2/2011 | Stack et al. |
| 7,899,554 B2 | 3/2011 | Williams et al. |
| 7,904,151 B2 | 3/2011 | Ben-David et al. |
| 7,904,176 B2 | 3/2011 | Ben-Ezra et al. |
| 7,908,008 B2 | 3/2011 | Ben-David et al. |
| 7,919,162 B2 | 4/2011 | Desimone et al. |
| 7,925,352 B2 | 4/2011 | Stack et al. |
| 7,949,400 B2 | 5/2011 | Kieval et al. |
| 7,953,481 B1 | 5/2011 | Shemer et al. |
| 7,966,067 B2 | 6/2011 | Rousso et al. |
| 7,974,693 B2 | 7/2011 | Ben-David et al. |
| 8,000,793 B2 | 8/2011 | Libbus |
| 8,005,542 B2 | 8/2011 | Ben-Ezra et al. |
| 8,005,545 B2 | 8/2011 | Ben-David et al. |
| 8,014,858 B1 | 9/2011 | Ben-haim et al. |
| 8,014,874 B2 | 9/2011 | Rossing et al. |
| 8,024,050 B2 | 9/2011 | Libbus et al. |
| 8,027,724 B2 | 9/2011 | Wei et al. |
| 8,032,215 B2 | 10/2011 | Libbus et al. |
| 8,036,745 B2 | 10/2011 | Ben-David et al. |
| 8,060,197 B2 | 11/2011 | Ben-David et al. |
| 8,060,206 B2 | 11/2011 | Kieval et al. |
| 8,060,218 B2 | 11/2011 | Singh et al. |
| 8,086,314 B1 | 12/2011 | Kieval |
| 8,116,881 B2 | 2/2012 | Cohen et al. |
| 8,116,883 B2 | 2/2012 | Williams et al. |
| 8,118,751 B2 | 2/2012 | Dobak, III |
| 8,121,693 B2 | 2/2012 | Libbus |
| 8,126,560 B2 | 2/2012 | Schiener et al. |
| 8,131,373 B2 | 3/2012 | Libbus |
| 8,145,304 B2 | 3/2012 | Moffitt et al. |
| 8,150,521 B2 | 4/2012 | Crowley et al. |
| 8,152,843 B2 | 4/2012 | Williams et al. |
| 8,155,744 B2 | 4/2012 | Rezai |
| 8,175,705 B2 | 5/2012 | Libbus |
| 8,195,289 B2 | 6/2012 | Heil, Jr. et al. |
| 8,195,290 B2 | 6/2012 | Brockway et al. |
| 8,204,591 B2 | 6/2012 | Ben-David et al. |
| 8,204,596 B2 | 6/2012 | Ransbury et al. |
| 8,206,456 B2 | 6/2012 | Stack et al. |
| 8,224,444 B2 | 7/2012 | Ben-David et al. |
| 8,229,564 B2 | 7/2012 | Rezai |
| 8,239,037 B2 | 8/2012 | Glenn et al. |
| 8,239,045 B2 | 8/2012 | Ransbury et al. |
| 8,244,355 B2 | 8/2012 | Bennett et al. |
| 8,249,706 B2 | 8/2012 | Koh |
| 8,260,416 B2 | 9/2012 | Ben-haim et al. |
| 8,290,595 B2 | 10/2012 | Kieval et al. |
| 8,301,247 B2 | 10/2012 | Ben-haim et al. |
| 8,306,616 B2 | 11/2012 | Ben-haim et al. |
| 8,306,617 B2 | 11/2012 | Ben-haim et al. |
| 8,311,629 B2 | 11/2012 | Ben-haim et al. |
| 8,311,633 B2 | 11/2012 | Ransbury et al. |
| 8,321,013 B2 | 11/2012 | Darvish et al. |
| 8,326,416 B2 | 12/2012 | Mika et al. |
| 8,335,571 B2 | 12/2012 | Singh et al. |
| 8,352,031 B2 | 1/2013 | Rousso et al. |
| 8,369,954 B2 | 2/2013 | Stack et al. |
| 8,372,325 B2 | 2/2013 | Williams et al. |
| 8,386,053 B2 | 2/2013 | Kornet |
| 8,386,056 B2 | 2/2013 | Ben-David et al. |
| 8,401,672 B2 | 3/2013 | Libbus et al. |
| 8,406,864 B2 | 3/2013 | Rousso et al. |
| 8,406,877 B2 | 3/2013 | Smith et al. |
| 8,412,326 B2 | 4/2013 | Arcot-Krishnamurthy et al. |
| 8,417,354 B2 | 4/2013 | Zhang et al. |
| 8,428,730 B2 | 4/2013 | Stack et al. |
| 8,437,867 B2 | 5/2013 | Murney et al. |
| 8,452,398 B2 | 5/2013 | Libbus et al. |
| 8,473,076 B2 | 6/2013 | Libbus et al. |
| 8,498,703 B2 | 7/2013 | Spinelli et al. |
| 8,538,535 B2 | 9/2013 | Gross et al. |
| 8,548,583 B2 | 10/2013 | Rousso et al. |
| 8,565,896 B2 | 10/2013 | Ben-David et al. |
| 8,571,651 B2 | 10/2013 | Ben-Ezra et al. |
| 8,571,653 B2 | 10/2013 | Ben-David et al. |
| 8,583,236 B2 | 11/2013 | Kieval et al. |
| 8,606,359 B2 | 12/2013 | Rossing et al. |
| 8,609,082 B2 | 12/2013 | Ben-David et al. |

(56) References Cited

U.S. PATENT DOCUMENTS

| | | |
|---|---|---|
| 8,615,294 B2 | 12/2013 | Ben-David et al. |
| 8,620,426 B2 | 12/2013 | Moffitt et al. |
| 8,626,290 B2 | 1/2014 | Dagan et al. |
| 8,626,299 B2 | 1/2014 | Gross et al. |
| 8,634,921 B2 | 1/2014 | Chavan et al. |
| 8,639,332 B2 | 1/2014 | Kuhn et al. |
| 8,655,444 B2 | 2/2014 | Ben-haim et al. |
| 8,682,430 B2 | 3/2014 | Libbus et al. |
| 8,682,434 B2 | 3/2014 | Libbus |
| 8,706,230 B2 | 4/2014 | Rousso et al. |
| 8,712,531 B2 | 4/2014 | Kieval et al. |
| 8,718,789 B2 | 5/2014 | Bolea et al. |
| 8,725,250 B2 | 5/2014 | Brockway et al. |
| 8,755,907 B2 | 6/2014 | Kieval et al. |
| 8,771,337 B2 | 7/2014 | Williams et al. |
| 8,784,354 B2 | 7/2014 | Stack et al. |
| 8,784,500 B2 | 7/2014 | Stack et al. |
| 8,788,066 B2 | 7/2014 | Cates et al. |
| 8,798,738 B2 | 8/2014 | Machado et al. |
| 8,805,501 B2 | 8/2014 | Libbus |
| 8,818,501 B2 | 8/2014 | Machado et al. |
| 8,825,152 B2 | 9/2014 | Shemer et al. |
| 8,838,246 B2 | 9/2014 | Kieval |
| 8,855,783 B2 | 10/2014 | Dagan et al. |
| 8,880,190 B2 | 11/2014 | Kieval et al. |
| 8,886,340 B2 | 11/2014 | Williams et al. |
| 8,901,878 B2 | 12/2014 | Prutchi et al. |
| 8,906,286 B2 | 12/2014 | Desimone et al. |
| 8,918,172 B2 | 12/2014 | Moffitt et al. |
| 8,929,990 B2 | 1/2015 | Moffitt et al. |
| 8,934,956 B2 | 1/2015 | Glenn et al. |
| 8,934,968 B2 | 1/2015 | Whitehurst et al. |
| 8,958,872 B2 | 2/2015 | Ben-haim et al. |
| 8,972,015 B2 | 3/2015 | Stack et al. |
| 8,977,353 B2 | 3/2015 | Rousso et al. |
| 8,983,601 B2 | 3/2015 | Fukamachi et al. |
| 9,005,100 B2 | 4/2015 | Gnanashanmugam et al. |
| 9,005,106 B2 | 4/2015 | Gross et al. |
| 9,011,751 B2 | 4/2015 | Williams et al. |
| 9,031,650 B2 | 5/2015 | McCabe et al. |
| 9,031,669 B2 | 5/2015 | Zhang et al. |
| 9,044,609 B2 | 6/2015 | Bolea et al. |
| 9,067,071 B2 | 6/2015 | Sanders et al. |
| 9,126,048 B2 | 9/2015 | Ransbury et al. |
| 9,149,639 B2 | 10/2015 | Zhang et al. |
| 9,168,094 B2 | 10/2015 | Lee et al. |
| 9,180,035 B2 | 11/2015 | Stack et al. |
| 9,186,514 B2 | 11/2015 | Ben-haim et al. |
| 9,216,289 B2 | 12/2015 | Libbus et al. |
| 9,248,038 B2 | 2/2016 | Stack et al. |
| 9,289,618 B1 | 3/2016 | Ben-haim et al. |
| 9,446,240 B2 | 9/2016 | Masson et al. |
| 9,480,790 B2 | 11/2016 | Machado et al. |
| 9,494,960 B2 | 11/2016 | Weerakoon et al. |
| 9,504,833 B2 | 11/2016 | Kramer et al. |
| 9,511,229 B2 | 12/2016 | Bradley |
| 9,517,350 B2 | 12/2016 | Ternes et al. |
| 9,545,512 B2 | 1/2017 | Williams et al. |
| 9,597,515 B2 | 3/2017 | Rockweiler et al. |
| 9,610,012 B2 | 4/2017 | Bardy |
| 9,622,665 B2 | 4/2017 | Zhang et al. |
| 9,623,252 B2 | 4/2017 | Sathaye et al. |
| 9,636,503 B2 | 5/2017 | Mokelke et al. |
| 9,656,089 B2 | 5/2017 | Yip et al. |
| 9,687,653 B2 | 6/2017 | Woods et al. |
| 9,707,076 B2 | 7/2017 | Stack et al. |
| 9,717,899 B2 | 8/2017 | Kuzma et al. |
| 9,731,135 B2 | 8/2017 | Arcot-Krishnamurthy et al. |
| 9,737,228 B2 | 8/2017 | Mahajan et al. |
| 9,782,591 B2 | 10/2017 | Kramer et al. |
| 9,814,883 B2 | 11/2017 | Marnfeldt et al. |
| 9,833,608 B2 | 12/2017 | Masson |
| 9,844,453 B2 | 12/2017 | Stack et al. |
| 9,848,795 B2 | 12/2017 | Marecki et al. |
| 9,849,290 B2 | 12/2017 | Zhao et al. |
| 9,855,317 B2 | 1/2018 | Bright |
| 9,861,435 B2 | 1/2018 | Richardson et al. |
| 9,878,150 B2 | 1/2018 | Machado et al. |
| 9,884,182 B2 | 2/2018 | Ransbury et al. |
| 10,172,549 B2 | 1/2019 | Waldhauser et al. |
| 10,188,343 B2 | 1/2019 | Goedeke et al. |
| 2002/0087192 A1 | 7/2002 | Barrett et al. |
| 2003/0045909 A1 | 3/2003 | Gross et al. |
| 2003/0114739 A1 | 6/2003 | Fuimaono et al. |
| 2003/0114878 A1 | 6/2003 | Diederich et al. |
| 2003/0216792 A1 | 11/2003 | Levin et al. |
| 2003/0233099 A1 | 12/2003 | Danaek et al. |
| 2004/0098090 A1 | 5/2004 | Williams et al. |
| 2004/0143254 A1 | 7/2004 | Vanney et al. |
| 2004/0172079 A1 | 9/2004 | Chinchoy |
| 2004/0172094 A1 | 9/2004 | Cohen et al. |
| 2004/0181136 A1 | 9/2004 | McDaniel et al. |
| 2004/0193231 A1 | 9/2004 | David et al. |
| 2004/0215233 A1 | 10/2004 | Kaplan et al. |
| 2004/0260375 A1 | 12/2004 | Zhang et al. |
| 2005/0065553 A1 | 3/2005 | Ben Ezra et al. |
| 2005/0119752 A1 | 6/2005 | Williams et al. |
| 2005/0142315 A1 | 6/2005 | Desimone et al. |
| 2005/0154321 A1 | 7/2005 | Wolinsky et al. |
| 2005/0187556 A1 | 8/2005 | Stack et al. |
| 2005/0187586 A1 | 8/2005 | David et al. |
| 2005/0187615 A1 | 8/2005 | Williams et al. |
| 2005/0197675 A1 | 9/2005 | David et al. |
| 2005/0247320 A1 | 11/2005 | Stack et al. |
| 2005/0251239 A1 | 11/2005 | Wallace et al. |
| 2005/0267542 A1 | 12/2005 | David et al. |
| 2005/0271794 A1 | 12/2005 | Desimone et al. |
| 2005/0273146 A1 | 12/2005 | Desimone et al. |
| 2006/0058597 A1 | 3/2006 | Machado et al. |
| 2006/0074453 A1 | 4/2006 | Kieval et al. |
| 2006/0085046 A1 | 4/2006 | Rezai et al. |
| 2006/0100668 A1 | 5/2006 | Ben-David et al. |
| 2006/0116737 A1 | 6/2006 | Libbus |
| 2006/0206159 A1 | 9/2006 | Moffitt et al. |
| 2006/0229677 A1 | 10/2006 | Moffitt et al. |
| 2006/0259084 A1 | 11/2006 | Zhang et al. |
| 2006/0259085 A1 | 11/2006 | Zhang et al. |
| 2007/0023951 A1 | 2/2007 | Williams et al. |
| 2007/0027527 A1 | 2/2007 | Williams et al. |
| 2007/0060932 A1 | 3/2007 | Stack et al. |
| 2007/0135875 A1 | 6/2007 | Demarais et al. |
| 2007/0255364 A1 | 11/2007 | Gerber et al. |
| 2008/0015659 A1 | 1/2008 | Zhang et al. |
| 2008/0046016 A1 | 2/2008 | Ben-David et al. |
| 2008/0082137 A1 | 4/2008 | Kieval et al. |
| 2008/0086182 A1 | 4/2008 | Ben-David et al. |
| 2008/0091240 A1 | 4/2008 | Ben-David et al. |
| 2008/0091241 A1 | 4/2008 | Ben-Ezra et al. |
| 2008/0091245 A1 | 4/2008 | Ben-Ezra et al. |
| 2008/0119898 A1 | 5/2008 | Ben-David et al. |
| 2008/0125819 A1 | 5/2008 | Ben-David et al. |
| 2008/0125825 A1 | 5/2008 | Ben-Ezra et al. |
| 2008/0125827 A1 | 5/2008 | Ben-David et al. |
| 2008/0125843 A1 | 5/2008 | Ben-David et al. |
| 2008/0132964 A1 | 6/2008 | Cohen et al. |
| 2008/0132983 A1 | 6/2008 | Cohen et al. |
| 2008/0140141 A1 | 6/2008 | Ben-David et al. |
| 2008/0161894 A1 | 7/2008 | Ben-David et al. |
| 2008/0167693 A1 | 7/2008 | Kieval et al. |
| 2008/0177338 A1 | 7/2008 | Ben-David et al. |
| 2008/0215008 A1 | 9/2008 | Nance et al. |
| 2008/0275349 A1 | 11/2008 | Halperin et al. |
| 2008/0275514 A1 | 11/2008 | Ben-David et al. |
| 2008/0312711 A1 | 12/2008 | Struble |
| 2009/0012542 A1 | 1/2009 | N'diaye et al. |
| 2009/0012546 A1 | 1/2009 | N'diaye et al. |
| 2009/0018596 A1 | 1/2009 | Kieval |
| 2009/0022078 A1 | 1/2009 | Zhang et al. |
| 2009/0096137 A1 | 4/2009 | Williams et al. |
| 2009/0105823 A1 | 4/2009 | Williams et al. |
| 2009/0163912 A1 | 6/2009 | Wang et al. |
| 2009/0228078 A1 | 9/2009 | Zhang et al. |
| 2009/0276022 A1 | 11/2009 | Burnes et al. |
| 2009/0281608 A1 | 11/2009 | Foster |

(56) References Cited

U.S. PATENT DOCUMENTS

| | | |
|---|---|---|
| 2010/0069768 A1 | 3/2010 | Min et al. |
| 2010/0222832 A1 | 9/2010 | Zhang et al. |
| 2011/0004198 A1 | 1/2011 | Hoch |
| 2011/0106199 A1 | 5/2011 | McCabe et al. |
| 2011/0118726 A1 | 5/2011 | de la Rama et al. |
| 2011/0153030 A1 | 6/2011 | Stack et al. |
| 2011/0160790 A1 | 6/2011 | Stegemann et al. |
| 2012/0029510 A1 | 2/2012 | Haverkost |
| 2012/0197141 A1 | 8/2012 | Vanney et al. |
| 2012/0232563 A1 | 9/2012 | Williams et al. |
| 2012/0253280 A1 | 10/2012 | Pantin et al. |
| 2012/0303080 A1 | 11/2012 | Ben-David et al. |
| 2012/0310304 A1 | 12/2012 | Brockway et al. |
| 2013/0012863 A1 | 1/2013 | Stack et al. |
| 2013/0110208 A1 | 5/2013 | Inagaki et al. |
| 2013/0172715 A1 | 7/2013 | Just et al. |
| 2013/0172953 A1 | 7/2013 | Machado et al. |
| 2013/0218221 A1 | 8/2013 | Zhang et al. |
| 2013/0226272 A1 | 8/2013 | Cattaneo et al. |
| 2013/0253616 A1 | 9/2013 | Libbus et al. |
| 2013/0289358 A1 | 10/2013 | Melsky et al. |
| 2013/0289686 A1 | 10/2013 | Masson et al. |
| 2013/0331919 A1 | 12/2013 | Zhang et al. |
| 2013/0338748 A1 | 12/2013 | Dagan |
| 2014/0012242 A1 | 1/2014 | Lee et al. |
| 2014/0046407 A1 | 2/2014 | Ben-Ezra et al. |
| 2014/0052208 A1 | 2/2014 | Ransbury et al. |
| 2014/0074148 A1 | 3/2014 | Glenn et al. |
| 2014/0114377 A1 | 4/2014 | Dagan et al. |
| 2014/0128750 A1 | 5/2014 | Ransbury et al. |
| 2014/0172006 A1 | 6/2014 | Stack et al. |
| 2014/0214135 A1 | 7/2014 | Ben-David et al. |
| 2014/0222031 A1 | 8/2014 | Stack et al. |
| 2014/0222125 A1 | 8/2014 | Glenn et al. |
| 2014/0277235 A1 | 9/2014 | An et al. |
| 2014/0324115 A1 | 10/2014 | Ziegler et al. |
| 2015/0018908 A1 | 1/2015 | Williams et al. |
| 2015/0039058 A1 | 2/2015 | Masson et al. |
| 2015/0066133 A1 | 3/2015 | Desimone et al. |
| 2015/0105645 A1 | 4/2015 | Subramaniam et al. |
| 2015/0134019 A1 | 5/2015 | Moffitt et al. |
| 2015/0142011 A1 | 5/2015 | Cates et al. |
| 2015/0150508 A1 | 6/2015 | Glenn et al. |
| 2015/0151121 A1 | 6/2015 | Dagan et al. |
| 2015/0157777 A1 | 6/2015 | Tuval et al. |
| 2015/0164662 A1 | 6/2015 | Tuval |
| 2015/0238763 A1 | 8/2015 | Bolea et al. |
| 2015/0306395 A1 | 10/2015 | Libbus et al. |
| 2016/0022890 A1 | 1/2016 | Schwammenthal et al. |
| 2016/0051741 A1 | 2/2016 | Schwammenthal et al. |
| 2016/0174864 A1 | 6/2016 | Levin et al. |
| 2017/0001015 A1 | 1/2017 | Marnfeldt et al. |
| 2017/0027458 A1 | 2/2017 | Glover et al. |
| 2017/0036014 A1 | 2/2017 | Machado et al. |
| 2017/0065812 A1 | 3/2017 | Goedeke et al. |
| 2017/0065818 A1 | 3/2017 | Ransbury et al. |
| 2017/0143227 A1 | 5/2017 | Marecki et al. |
| 2017/0173338 A1 | 6/2017 | Waldhauser et al. |
| 2017/0173339 A1 | 6/2017 | Waldhauser et al. |
| 2017/0189642 A1 | 7/2017 | Masson et al. |
| 2017/0224999 A1 | 8/2017 | Yip et al. |
| 2017/0258337 A1 | 9/2017 | Libbus et al. |
| 2017/0291023 A1 | 10/2017 | Kuzma et al. |
| 2017/0296086 A1 | 10/2017 | Ternes et al. |
| 2017/0312525 A1 | 11/2017 | Masson et al. |
| 2017/0325881 A1 | 11/2017 | Richardson et al. |
| 2018/0050190 A1 | 2/2018 | Masson |
| 2018/0147408 A1 | 5/2018 | Machado et al. |
| 2018/0161577 A1 | 6/2018 | Goedeke et al. |
| 2018/0168503 A1 | 6/2018 | Waldhauser et al. |
| 2018/0169414 A1 | 6/2018 | Goedeke et al. |
| 2018/0214696 A1 | 8/2018 | Cuchiara et al. |
| 2018/0214697 A1 | 8/2018 | Cuchiara et al. |
| 2018/0214698 A1 | 8/2018 | Cuchiara et al. |
| 2018/0236220 A1 | 8/2018 | Glenn et al. |

FOREIGN PATENT DOCUMENTS

| | | |
|---|---|---|
| EP | 2 316 525 | 1/2016 |
| JP | 2001-505450 | 4/2001 |
| JP | 2004-160219 | 6/2004 |
| JP | 2008-526456 | 7/2008 |
| JP | 2009-508594 | 3/2009 |
| JP | 2011-147791 | 8/2011 |
| WO | WO 1997/024983 | 7/1997 |
| WO | WO 2005/041748 | 5/2005 |
| WO | WO 2006/058253 | 6/2006 |
| WO | WO 2007/052341 | 5/2007 |
| WO | WO 2008/054448 | 5/2008 |
| WO | WO 2009/135083 | 11/2009 |
| WO | WO 2012/068273 | 5/2012 |
| WO | WO 2012/149511 | 11/2012 |
| WO | WO 2016/195477 | 12/2016 |
| WO | WO 2017/156039 | 9/2017 |

OTHER PUBLICATIONS

Casadei, "Vagal control of myocardial . . . in humans," The Physiological Society (Mar. 2001): 817-823.

De Ferrari et al., "Vagus nerve stimulation . . . future directions," Heart Fail Rev. (2011) 16: 195-203.

Klein et al., "Vagus nerve stimulation . . . heart failure," Cariology Journal (2010) 17 (6): 638-643.

Koizumi et al., "Functional significance of coactivation . . . ," National Academy of Sciences (Mar. 1982) 79 (6): 2116-2120.

Lawo et al., "Electrical Signals Applied During the Absolute Refractory Period", JACC, Dec. 20, 2005, vol. 46, No. 21, pp. 2229-2236.

Meyer et al., "Augmentation of left ventricular . . . ," Americ. Heart Assoc. (2010): 1286-1294.

Murphy, "Preliminary observations of the effects of simulation of . . . in man," CA Journal of Phys. and Pharmac (Jun. 1985). 63 (6): 649-655.

Randall et al., "Regional cardiac distribution . . . ," Federation Proceedings (Jul.-Aug. 1972) 31 (4): 1199-1208.

Randall, "Augmentor action to the sympathetic . . . ," Journal of Applied Physiology (Jul. 1960) 15 (4): 629-631.

Rudski et al., "Guidelines for the Echocardiographic Assessment of the Right Heart in Adults: A Report from the American Society of Echocardiography", J Am Soc Echocardiogr, 2010, vol. 23, pp. 685-713.

Triposkiadis et al., "Sympathetic nervous . . . failure," Journal of Amer. Coll. of Cardiology (Nov. 3, 2009) 54 (19): 1747-1762.

Zarse, "Selective increase . . . sympathetic tone," Journal of Amer. Coll. of Cardiology (2005) 46 (7): 1354-1359.

International Search Report and Written Opinion issued in PCT Application No. PCT/US2016/012082, dated Apr. 28, 2016, in 17 pages.

Fornell, "Multi-Electrode RF Balloon Efficient for Acute Pulmonary Vein Isolation", Ablation Systems, May 17, 2017, http://www.dicardiology.com/article/multi-electrode-rf-balloon-efficient-acute-pulmonary-vein-isolation?sthash.wVTUprlW.mjjo, downloaded on Oct. 30, 2017.

Karamanoglu, "A System for Analysis of Arterial Blood Pressure Waveforms in Humans", Computers and Biomedical Research, 1997, vol. 30, pp. 244-255.

Karamanoglu et al., "Estimation of cardiac output in patients with congestive heart failure by analysis of right ventricular pressure waveforms", Biomedical Engineering Online, 2011, vol. 10, No. 36.

Karamanoglu et al., "Right Ventricular Pressure Waveform and Wave Reflection Analysis in Patients With Pulmonary Arterial Hypertension", Chest Jour., Jul. 2007, vol. 132, No. 1, pp. 37-43.

CARDIAC MODULATION FACILITATION METHODS AND SYSTEMS

INCORPORATION BY REFERENCE TO ANY PRIORITY APPLICATIONS

The present application claims priority benefit of U.S. Provisional Patent App. No. 62/099,834, filed Jan. 5, 2015. That application is hereby incorporated by reference in its entirety.

BACKGROUND

Field

The present disclosure relates generally to methods and systems for facilitating modulation (e.g., electrical neuromodulation), and more particularly to methods and systems for facilitating therapeutic and calibration electrical neuromodulation of one or more nerves in and around the heart.

Description of the Related Art

Acute heart failure is a cardiac condition in which a problem with the structure or function of the heart impairs its ability to supply sufficient blood flow to meet the body's needs. The condition impairs quality of life and is a leading cause of hospitalizations and mortality in the western world. Treating acute heart failure is typically aimed at removal of precipitating causes, prevention of deterioration in cardiac function, and control of the patient's congestive state.

SUMMARY

Treatments for acute heart failure include the use of inotropic agents, such as dopamine and dobutamine. These agents, however, have both chronotropic and inotropic effects and characteristically increase heart contractility at the expense of significant increases in oxygen consumption secondary to elevations in heart rate. As a result, although these inotropic agents increase myocardial contractility and improve hemodynamics, clinical trials have consistently demonstrated excess mortality caused by cardiac arrhythmias and increase in myocardium consumption.

As such, there is a need for selectively and locally treating acute heart failure and otherwise achieving hemodynamic control without causing unwanted systemic effects. Accordingly, in some embodiments, no inotropics are used. In other embodiments, reduced dosages of inotropics may be used because, for example, synergistic effects are provided through various embodiments herein. By reducing the dosages, the side effects can also be significantly reduced.

Several embodiments of the present disclosure provide for methods of tissue modulation, such as neuromodulation, for cardiac and other disorders. For example, some embodiments provide methods and devices for neuromodulation of one or more nerves in and around a heart of a patient. Several methods of the present disclosure, for example, may be useful in electrical neuromodulation of patients with cardiac disease, such as patients with acute or chronic cardiac disease. Several methods of the present disclosure encompass, for example, neuromodulation of one or more target sites of the autonomic nervous system of the heart, where sensed non-electrical heart activity properties are used in making adjustments to one or more properties of the electrical pulses delivered to the patient. Non-limiting examples of medical conditions that can be treated according to the present disclosure include cardiovascular medical conditions.

Several methods of the present disclosure allow for electrical neuromodulation of the heart of the patient, for example including delivering one or more electrical pulses through a catheter positioned in a pulmonary artery of the heart of the patient, sensing from at least a first sensor positioned at a first location within the vasculature of the heart one or more heart activity properties (e.g., a non-electrical heart activity property) in response to the one or more electrical pulses, and adjusting a property of the one or more electrical pulses delivered through the catheter positioned in the pulmonary artery of the heart in response to the one or more heart activity properties. The methods may provide adjuvant cardiac therapy to the patient.

Sensing from at least the first sensor positioned at the first location can include sensing one or more of a pressure property, an acceleration property, an acoustic property, a temperature, and a blood chemistry property from within the vasculature of the heart. Among other locations, the first sensor can be positioned in one of a left pulmonary artery, a right pulmonary artery, a pulmonary artery branch vessel, or a pulmonary trunk of the heart. The one or more electrical pulses can optionally be delivered through the catheter positioned in one of the left pulmonary artery, the right pulmonary artery, or pulmonary trunk of the heart that does not contain the first sensor. The first sensor can also be positioned in a pulmonary trunk of the heart.

Other locations for the first sensor can include in the right ventricle of the heart and in the right atrium of the heart. When positioned in the right atrium of the heart, the first sensor can optionally be positioned on the septal wall of the right atrium of the heart. The first sensor could also be positioned on the septal wall of the right ventricle. The right ventricle and the left ventricle share a septal wall, so a sensor in the right ventricle or on the septal wall of the right ventricle may be preferable for detecting properties indicative of left ventricle contractility or cardiac output. Additional locations for positioning the first sensor include in a superior vena cava of the heart, the inferior vena cava of the heart, and in a coronary sinus of the heart. When positioned in the coronary sinus of the heart, the first sensor can be used to sense at least one of a temperature or a blood oxygen level.

In some embodiments, the first sensor may be positioned in the left atrium (e.g., by forming an aperture in the septal wall between the right atrium and the left atrium, or by using a patent foramen ovale (PFO) or atrial septal defect (ASD)). A sensor in the left atrium may be useful for detecting properties indicative of the left ventricle. If the left atrium has been accessed, in some embodiments, the sensor may be positioned in the left ventricle itself, which may provide the most direct measurement of properties associated with the left ventricle. In some embodiments, the sensor may be positioned downstream of the left ventricle, including the aorta, aortic branch arteries, etc. When the procedure is complete, any aperture that was created or existing may be closed using a closure device such as Amplatzer, Helex, CardioSEAL, or others.

Some methods can include sensing one or more cardiac properties from a skin surface of the patient, and adjusting the property of the one or more electrical pulses delivered through the catheter positioned in the pulmonary artery of the heart in response to the one or more heart activity properties (e.g., non-electrical properties) from the first sensor positioned at a first location within the vasculature of the heart and/or the one or more cardiac properties from the skin surface of the patient. The one or more cardiac properties sensed from the skin surface of the patient can include, for example, an electrocardiogram property.

Some methods can include sensing from at least a second sensor positioned at a second location within the vasculature of the heart one or more heart activity properties (e.g., non-electrical heart activity properties) in response to the one or more electrical pulses, and adjusting the property of the one or more electrical pulses delivered through the catheter positioned in the pulmonary artery of the heart in response to the one or more heart activity properties from the first sensor and/or the one or more heart activity properties from the second sensor.

Adjusting the property of the one or more electrical pulses can include a variety of responses. For example, adjusting the property of the one or more electrical pulses can include changing which of an electrode or plurality of electrodes on the catheter is used to deliver the one or more electrical pulses. For another example, adjusting the property of the one or more electrical pulses can include moving the catheter to reposition one or more electrodes of the catheter in the pulmonary artery of the heart. For yet another example, adjusting the property of the one or more electrical pulses can include changing at least one of an electrode polarity, a pulsing mode, a pulse width, an amplitude, a frequency, a phase, a voltage, a current, a duration, an inter-pulse interval, a duty cycle, a dwell time, a sequence, a wavelength, and/or a waveform of the one or more electrical pulses.

A hierarchy of electrode configurations can be assigned from which to deliver the one or more electrical pulses. The one or more electrical pulses can be delivered based on the hierarchy of electrode configurations, where the one or more heart activity properties sensed in response to the one or more electrical pulses can be analyzed and an electrode configuration can be selected to use for delivering the one or more electrical pulses through the catheter positioned in the pulmonary artery of a heart of a patient based on the analysis. A hierarchy can be assigned to each property of the one or more electrical pulses delivered through the catheter positioned in the pulmonary artery of the heart, where the one or more electrical pulses are delivered based on the hierarchy of each property. The one or more non-electrical heart activity properties sensed in response to the one or more electrical pulses are analyzed and an electrode configuration can be selected to be used for delivering the one or more electrical pulses through the catheter positioned in the pulmonary artery of a heart of a patient based on the analysis. Analyzing the one or more heart activity properties can include analyzing a predetermined number of the one or more heart activity properties.

In some embodiments, a method of facilitating therapeutic neuromodulation of a heart of a patient comprises positioning an electrode in a pulmonary artery of a heart and positioning a sensor in a right ventricle of the heart. The method further comprises delivering, via a stimulation system, a first series of electrical signals to the electrode. The first series comprises a first plurality of electrical signals. Each of the first plurality of electrical signals comprises a plurality of parameters. Each of the first plurality of electrical signals of the first series only differs from one another by a magnitude of a first parameter of the plurality of parameters. The method further comprises, after delivering the first series of electrical signals to the electrode, delivering, via the stimulation system, a second series of electrical signals to the electrode. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters. The second parameter is different than the first parameter. The method further comprises determining, via the sensor, sensor data indicative of one or more non-electrical heart activity properties in response to delivering the first series of electrical signals and the second series of electrical signals, and delivering a therapeutic neuromodulation signal to the pulmonary artery using selected electrical parameters. The selected electrical parameters comprise a selected magnitude of the first parameter and a selected magnitude of the second parameter. The selected magnitudes of the first and second parameters are based at least partially on the sensor data. The therapeutic neuromodulation signal increases heart contractility more than heart rate.

The method may further comprise delivering, via the stimulation system, a third series of electrical signals to the electrode. The third series comprises a third plurality of electrical signals. Each of the third plurality of electrical signals comprises the plurality of parameters. Each of the third plurality of electrical signals of the third series only differs from one another by a magnitude of a third parameter of the plurality of parameters. The third parameter is different than the first parameter and the second parameter. The method may further comprise determining, via the sensor, sensor data indicative of the one or more non-electrical heart activity properties in response to delivering the third series of electrical signals. The selected electrical parameters may comprise a selected magnitude of the third parameter. The selected magnitude of the third parameter is based at least partially on the sensor data.

The method may further comprise determining a desired hierarchy between the first series and the second series. The pulmonary artery may comprise a right pulmonary artery. The one or more non-electrical heart activity properties may comprise at least one of a pressure property, an acceleration property, an acoustic property, a temperature, and a blood chemistry property. Determining the sensor data may comprise determining, via a second sensor on a skin surface, sensor data indicative of an electrocardiogram property in response to delivering the first series of electrical signals and the second series of electrical signals.

The first parameter may be one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform, and, optionally, the second parameter may be a different one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform. The second parameter may be one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform. The first parameter may comprise current and the second parameter may comprise a parameter relating to timing (e.g., one of frequency and duty cycle).

In some embodiments, a method of facilitating therapeutic neuromodulation of a heart of a patient comprises positioning an electrode in a pulmonary artery of a heart, positioning a sensor in a right ventricle of the heart, delivering, via a stimulation system, a first electrical signal of a series of electrical signals to the electrode, and, after delivering the first electrical signal, delivering, via the stimulation system, a second electrical signal of the series of electrical signals to the electrode. The second electrical signal differs from the first electrical signal by a magnitude of a first parameter of a plurality of parameters. The method further comprises determining, via the sensor, sensor data indicative of one or more non-electrical heart activity properties in response to the delivery of the series of electrical signals, and delivering a therapeutic neuromodulation signal to the pulmonary artery using selected electrical parameters. The selected electrical parameters comprise a selected magnitude of the first parameter. The selected magnitude of the first parameter is based at least partially on the sensor data. The therapeutic neuromodulation signal increases heart contractility more than heart rate.

The pulmonary artery may comprise a right pulmonary artery. The pulmonary artery may comprise a left pulmonary artery. The pulmonary artery may comprise a pulmonary trunk. The one or more non-electrical heart activity properties may comprise at least one of a pressure property, an acceleration property, an acoustic property, a temperature, and a blood chemistry property. Determining the sensor data may comprise determining, via a second sensor on a skin surface of the patient, sensor data indicative of an electrocardiogram property in response to delivering the series of electrical signals. The first parameter may be one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform.

In some embodiments, a method of facilitating therapeutic neuromodulation of a heart of a patient comprises delivering a first series of electrical signals to an electrode in a first anatomical location, and, after delivering the first series of electrical signals to the electrode, delivering a second series of electrical signals to the electrode. The first series comprises a first plurality of electrical signals. Each of the first plurality of electrical signals comprises a plurality of parameters. Each of the first plurality of electrical signals of the first series only differs from one another by a magnitude of a first parameter of the plurality of parameters. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters. The second parameter is different than the first parameter. The method further comprises sensing, via a sensor in a second anatomical location different than the first anatomical location, sensor data indicative of one or more non-electrical heart activity properties in response to delivering the first series of electrical signals and the second series of electrical signals, and providing a therapeutic neuromodulation signal to the first anatomical location using selected electrical parameters. The selected electrical parameters comprise a selected magnitude of the first parameter and a selected magnitude of the second parameter. The selected magnitudes of the first and second parameters are based at least partially on the sensor data. The therapeutic neuromodulation signal increases heart contractility.

The method may further comprise delivering a third series of electrical signals to the electrode. The third series comprises a third plurality of electrical signals. Each of the third plurality of electrical signals comprises the plurality of parameters. Each of the third plurality of electrical signals of the third series only differs from one another by a magnitude of a third parameter of the plurality of parameters. The third parameter is different than the first parameter and the second parameter. The method may further comprise sensing, via the sensor, sensor data indicative of the one or more non-electrical heart activity properties in response to delivering the third series of electrical signals. The selected electrical parameters may comprise a selected magnitude of the third parameter. The selected magnitude of the third parameter is based at least partially on the sensor data.

The method may further comprise determining a desired hierarchy between the first series and the second series. The first anatomical location may comprise a right pulmonary artery. The pulmonary artery may comprise a left pulmonary artery. The pulmonary artery may comprise a pulmonary trunk. The one or more non-electrical heart activity properties may comprise at least one of a pressure property, an acceleration property, an acoustic property, a temperature, and a blood chemistry property. Sensing the sensor data may comprise determining, via a second sensor on a skin surface, sensor data indicative of an electrocardiogram property in response to delivering the first series of electrical signals and the second series of electrical signals.

The first parameter may one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform, and, optionally, the second parameter may be a different one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform. The second parameter may one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform. The first parameter may comprise current and the second parameter may comprise a parameter related to timing (e.g., one of frequency and duty cycle).

In some embodiments, a method of facilitating therapeutic neuromodulation of a heart of a patient comprises delivering a first electrical signal of a series of electrical signals to an electrode in a first anatomical location, and, after delivering the first electrical signal, delivering a second electrical signal of the series of electrical signals to the electrode. The second electrical signal differs from the first electrical signal by a magnitude of a first parameter of a plurality of parameters. The method further comprises sensing, via a sensor in a second anatomical location different than the first anatomical location, sensor data indicative of one or more non-electrical heart activity properties in response to the delivery of the series of electrical signals, and providing a therapeutic neuromodulation signal to the first anatomical location using selected electrical parameters. The selected electrical parameters comprise a selected magnitude of the first parameter. The selected magnitude of the first parameter is based at least partially on the sensor data. The therapeutic neuromodulation signal increases heart contractility.

The first anatomical location may comprise a right pulmonary artery. The first anatomical location may comprise a left pulmonary artery. The first anatomical location may comprise a pulmonary trunk. The one or more non-electrical heart activity properties may comprise at least one of a pressure property, an acceleration property, an acoustic property, a temperature, and a blood chemistry property. Sensing the sensor data may comprise sensing, via a second sensor on a skin surface of the patient, sensor data indicative of an electrocardiogram property in response to delivering the series of electrical signals. The first parameter may be one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform.

In some embodiments, a neuromodulation system for facilitating delivery of electric signals to a heart of a patient comprises a catheter and a stimulation system. The catheter comprises a catheter body comprising a proximal end, a distal end, a lumen extending from the proximal end towards the distal end, and an outer surface. The catheter further comprises an electrode on the outer surface. The electrode is configured to deliver an electrical signal to a pulmonary artery of a patient. The catheter further comprises a sensor on the outer surface. The sensor is configured to sense a heart activity property from a location within in vasculature of the patient. The stimulation system comprises a pulse generator configured to deliver a first series of electrical signals and a second series of electrical signals to the electrode. The first series comprises a first plurality of electrical signals. Each of the first plurality of electrical signals comprises a plurality of parameters. Each of the first plurality of electrical signals of the first series only differs from one another by a magnitude of a first parameter of the plurality of parameters. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters. The second parameter is different than the first parameter. The stimulation system further comprises a non-transitory computer-readable medium configured to store sensor data indicative of one or more non-electrical heart activity properties in response to delivering the first series of electrical signals and the second series of electrical signals to the electrode, and a processor configured to determine a selected magnitude of the first parameter and a selected magnitude of the second parameter based at least partially on the sensor data. The non-transitory computer readable medium is configured to store selected electrical parameters including the selected magnitude of the first parameter and the selected magnitude of the second parameter. The pulse generator is configured to deliver a therapeutic neuromodulation signal to the electrode using selected electrical parameters.

In some embodiments, a neuromodulation system for facilitating delivery/of electric signals to a heart of a patient comprises a catheter and a stimulation system. The catheter comprises a catheter body comprising a proximal end, a distal end, a lumen extending from the proximal end towards the distal end, and an outer surface. The catheter further comprises an electrode on the outer surface. The electrode is configured to deliver an electrical signal to a pulmonary artery of a patient. The catheter further comprises a sensor on the outer surface. The sensor is configured to sense a heart activity property from a location within in vasculature of the patient. The stimulation system comprises a pulse generator configured to deliver a series of electrical signals to the electrode. The series comprises a first electrical signal and a second electrical signal. The second electrical signal differs from the first electrical signal by a magnitude of a first parameter of a plurality of parameters. The stimulation system further comprises a non-transitory computer-readable medium configured to store sensor data indicative of one or more non-electrical heart activity properties in response to delivering the series of electrical signals to the electrode, and a processor configured to determine a selected magnitude of the first parameter based at least partially on the sensor data. The non-transitory computer readable medium is configured to store selected electrical parameters including the selected magnitude of the first parameter. The pulse generator is configured to deliver a therapeutic neuromodulation signal to the electrode using selected electrical parameters.

In some embodiments, a neuromodulation system for facilitating delivery of electric signals to a heart of a patient comprises a catheter and a shaping wire. The catheter comprises a catheter body comprising a proximal end, a distal end, a lumen extending from the proximal end towards the distal end, and an outer surface. The catheter further comprises an electrode on the outer surface. The electrode is configured to deliver an electrical signal to a pulmonary artery of a patient. The shaping wire is configured to be positioned in the lumen of the catheter body. The shaping wire comprises a bent portion. When the shaping wire is inserted in the lumen of the catheter body, the catheter body comprises a curved portion corresponding to the bent portion of the shaping wire.

The heart activity property may comprise a non-electrical hearty activity property. The non-electrical heart activity property may comprise at least one of a pressure property, an acceleration property, an acoustic property, a temperature, and a blood chemistry property. The electrode may be configured to deliver the electrical signal to a right pulmonary artery of the patient. The electrode may be configured to be positioned in a different location than the sensor. The catheter system may comprise a plurality of electrodes including the electrode. The location may be a pulmonary trunk, a right ventricle, a septal wall of a right ventricle, a right atrium, a septal wall of a right atrium, a superior vena cava, a pulmonary branch artery vessel, an inferior vena cava, or a coronary sinus. The neuromodulation system may further comprise a skin sensor configured to sense a cardiac property from a skin surface of the patient. The heart activity property may comprise a non-electrical heart activity property and wherein the cardiac property may comprise an electrical cardiac property. The electrical cardiac property may comprise an electrocardiogram property.

In some embodiments, a method of neuromodulation of a heart of a patient comprises positioning a catheter including an electrode in a pulmonary artery of a heart, positioning a sensor in a location within vasculature of the heart, delivering, via a stimulation system, a first set of one or more electrical pulses to the electrode, the first set of one or more electrical pulses having a first pulse property, and, after delivering the first delivering set of one or more electrical pulses to the electrode, delivering, via the stimulation system, a second set of one or more electrical pulses to the electrode. The second set of one or more electrical pulses has a second pulse property different than the first pulse property. The method further comprises delivering therapeutic electrical pulses to the pulmonary artery using an electrode configuration selected by analyzing one or more heart activity properties sensed, via the sensor, in response to the delivery of the first and second sets of electrical pulses. The electrode configuration comprises the first pulse property or the second pulse property based at least partially on the analysis. The therapeutic neuromodulation signal increases heart contractility more than heart rate.

In some embodiments, a method of modulation (e.g., electrical neuromodulation) of a heart of a patient comprises delivering one or more electrical pulses through a catheter positioned in a pulmonary artery of the heart of the patient, sensing from at least a first sensor positioned at a first location within a vasculature of the heart one or more non-electrical heart activity properties in response to the one or more electrical pulses, and adjusting a property of the one or more electrical pulses delivered through the catheter positioned in the pulmonary artery of the heart in response to the one or more non-electrical heart activity properties.

In some embodiments, sensing from at least the first sensor positioned at the first location may include sensing one or more of a pressure property, an acceleration property, an acoustic property, a temperature, and a blood chemistry property from within the vasculature of the heart.

In one embodiment, a first sensor is placed in one of a left pulmonary artery, a right pulmonary artery, or a pulmonary trunk of the heart. One or more electrical pulses are delivered through the catheter positioned in one of the left pulmonary artery, the right pulmonary artery, or the pulmonary trunk of the heart that does not contain the first sensor.

The first sensor may be positioned in the left pulmonary artery. The first sensor may be positioned in the right pulmonary artery. The first sensor may be positioned in other vessels in and around the heart, including, but not limited to, the pulmonary trunk, a pulmonary artery branch vessel, right ventricle, a septal wall of the right ventricle, a right atrium, the septal wall of the right atrium, a superior vena cava, an inferior vena cava or a coronary sinus The first sensor (e.g., in the coronary sinus) may sense at least one of a temperature or a blood oxygen level.

In several embodiments, the method may include sensing one or more cardiac properties from a skin surface of the patient and adjusting the property of the one or more electrical pulses delivered through the catheter positioned in the pulmonary artery of the heart in response to the one or more non-electrical heart activity properties and the one or more cardiac properties from the skin surface of the patient. The one or more cardiac properties sensed from the skin surface of the patient may include an electrocardiogram property. The may include sensing from at least a second sensor positioned at a second location within the vasculature of the heart one or more non-electrical heart activity properties in response to the one or more electrical pulses and adjusting the property of the one or more electrical pulses delivered through the catheter positioned in the pulmonary artery of the heart in response to the one or more non-electrical heart activity properties received by the first sensor and the second sensor. In several embodiments, adjusting the property of the one or more electrical pulses may include one or more of the following (i) changing which electrode on the catheter is used to deliver the one or more electrical pulses; (ii) moving the catheter to reposition electrodes of the catheter in the pulmonary artery of the heart; (iii) changing at least one of an electrode polarity, a pulsing mode, a pulse width, an amplitude, a frequency, a phase, a voltage, a current, a duration, an inter-pulse interval, a duty cycle, a dwell time, a sequence, a wavelength, or a waveform of the one or more electrical pulses.

In several embodiments, the method may include assigning a hierarchy of electrode configurations from which to deliver the one or more electrical pulses, delivering the one or more electrical pulses based at least partially on the hierarchy of electrode configurations, analyzing the one or more non-electrical heart activity properties sensed in response to the one or more electrical pulses, and selecting an electrode configuration to use for delivering the one or more electrical pulses through the catheter positioned in the pulmonary artery of a heart of a patient based at least partially on the analysis. The method may include assigning a hierarchy to each property of the one or more electrical pulses delivered through the catheter positioned in the pulmonary artery of the heart, delivering the one or more electrical pulses based at least partially on the hierarchy of each property, analyzing the one or more non-electrical heart activity properties sensed in response to the one or more electrical pulses, and selecting an electrode configuration to use for delivering the one or more electrical pulses through the catheter positioned in the pulmonary artery of a heart of a patient based at least partially on the analysis. Analyzing the one or more non-electrical heart activity properties may include analyzing a predetermined number of the one or more non-electrical heart activity properties.

In several embodiments, therapeutic neuromodulation is not provided. Instead, several embodiments are provided for the purposes of calibrating or optimizing a signal for, e.g., diagnosis or calibration purposes.

In some embodiments, a method of non-therapeutic calibration comprises positioning an electrode in a pulmonary artery of a heart and positioning a sensor in a right ventricle of the heart. The system further comprises delivering, via a stimulation system, a first series of electrical signals to the electrode. The first series comprises a first plurality of electrical signals. Each of the first plurality of electrical signals comprises a plurality of parameters. Each of the first plurality of electrical signals of the first series only differs from one another by a magnitude of a first parameter of the plurality of parameters. The method further comprises, after delivering the first series of electrical signals to the electrode, delivering, via the stimulation system, a second series of electrical signals to the electrode. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters. The second parameter is different than the first parameter. The method further comprises determining, via the sensor, sensor data indicative of one or more non-electrical heart activity properties in response to delivering the first series of electrical signals and the second series of electrical signals. The method further comprises determining a therapeutic neuromodulation signal to be delivered to the pulmonary artery using selected electrical parameters. The selected electrical parameters comprise a selected magnitude of the first parameter and a selected magnitude of the second parameter. The selected magnitudes of the first and second parameters are based at least partially on the sensor data.

In some embodiments, a method of non-therapeutic calibration comprises delivering a first electrical signal of a series of electrical signals to an electrode in a first anatomical location and, after delivering the first electrical signal, delivering a second electrical signal of the series of electrical signals to the electrode. The second electrical signal differs from the first electrical signal by a magnitude of a first parameter of a plurality of parameters. The method further comprises sensing, via a sensor in a second anatomical location different than the first anatomical location, sensor data indicative of one or more non-electrical heart activity properties in response to the delivery of the series of electrical signals, and determining a therapeutic neuromodulation signal to be delivered to the first anatomical location using selected electrical parameters. The selected electrical parameters comprise a selected magnitude of the first parameter. The selected magnitude of the first parameter is based at least partially on the sensor data.

The methods summarized above and set forth in further detail below describe certain actions taken by a practitioner; however, it should be understood that they can also include the instruction of those actions by another party. Thus, actions such as "positioning an electrode" include "instructing positioning of an electrode."

For purposes of summarizing the invention and the advantages that may be achieved, certain objects and advantages are described herein. Not necessarily all such objects or advantages need to be achieved in accordance with any particular embodiment. In some embodiments, the invention may be embodied or carried out in a manner that can achieve or optimize one advantage or a group of advantages without necessarily achieving other objects or advantages.

The embodiments disclosed herein are intended to be within the scope of the invention herein disclosed. These and other embodiments will be apparent from the following detailed description having reference to the attached figures, the invention not being limited to any particular disclosed embodiment(s). Optional and/or preferred features described with reference to some embodiments may be combined with and incorporated into other embodiments. All references cited herein, including patents and patent applications, are incorporated by reference in their entirety.

DETAILED DESCRIPTION

Figure 1A:
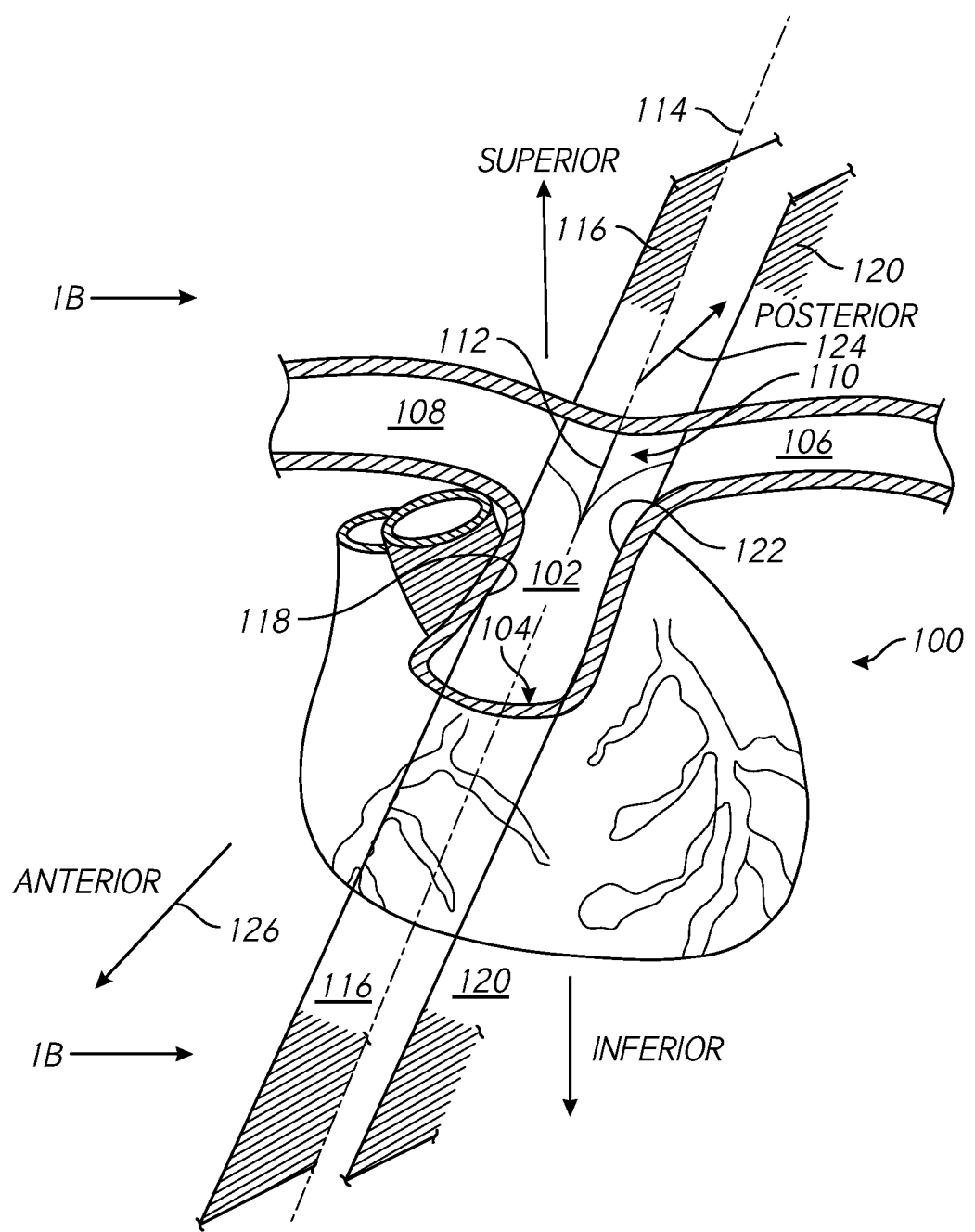
FIGS. 1A through 1C are schematic illustrations of a heart and surrounding areas from various perspectives.

Several embodiments of the present disclosure provide for methods and devices that can be used to apply electrical neuromodulation to one or more nerves in and around the heart of a patient. Several embodiments, for example, may be useful in electrical neuromodulation of patients with cardiovascular medical conditions, such as patients with acute or chronic cardiac disease. As discussed herein, several embodiments can allow for a portion of a catheter to be positioned within the vasculature of the patient in at least one of the right pulmonary artery, the left pulmonary artery, and the pulmonary trunk. Once positioned, an electrode system of the catheter can provide electrical pulses to stimulate the autonomic nervous system surrounding (e.g., proximate to) the pulmonary artery in an effort to provide adjuvant cardiac therapy to the patient. Sensed heart activity properties (e.g., non-electrical heart activity properties) can be used as the basis for making adjustments to one or more properties of the one or more electrical pulses delivered through the catheter positioned in the pulmonary artery of the heart in an effort to provide adjuvant cardiac therapy to the patient.

Certain groups of figures showing similar items follow a numbering convention in which the first digit or digits correspond to the drawing figure number and the remaining digits identify an element or component in the drawing. Similar elements or components between such groups of figures may be identified by the use of similar digits. For example, 110 may reference element "10" in FIG. 1, and a similar element "10" may be referenced as 210 in FIG. 2. As will be appreciated, elements shown in the various embodiments herein can be added, exchanged, and/or eliminated so as to provide any number of additional embodiments of the present disclosure.

The terms "distal" and "proximal" are used herein with respect to a position or direction relative to the treating clinician taken along the devices of the present disclosure. "Distal" or "distally" are a position distant from or in a direction away from the clinician taken along the catheter. "Proximal" and "proximally" are a position near or in a direction toward the clinician taken along the catheter.

In several embodiments, the catheters provided herein include a plurality of electrodes, which includes two or more electrodes. It is understood that the phrase "a plurality of electrodes" can be replaced herein with two or more electrodes if desired. With respect to treating cardiovascular medical conditions, such medical conditions can involve medical conditions related to the components of the cardiovascular system such as, for example, the heart and/or aorta. Non-limiting examples of cardiovascular conditions include post-infarction rehabilitation, shock (hypovolemic, septic, neurogenic), valvular disease, heart failure, angina, microvascular ischemia, myocardial contractility disorder, cardiomyopathy, hypertension including pulmonary hypertension and systemic hypertension, orthopnea, dyspenea, orthostatic hypotension, dysautonomia, syncope, vasovagal reflex, carotid sinus hypersensitivity, pericardial effusion, heart failure, and cardiac structural abnormalities such as septal defects and wall aneurysms.

In some embodiments, a catheter, for example as discussed herein, can be used in conjunction with a pulmonary artery catheter, such as a Swan-Ganz type pulmonary artery catheter, to deliver transvascular neuromodulation via the pulmonary artery to an autonomic target site to treat a cardiovascular condition. In certain such embodiments, the catheter is housed within one of the multiple lumens of a pulmonary artery catheter. Examples of catheters include those discussed herein and those disclosed in U.S. Provisional Patent Application No. 62/001,729, entitled "Catheter and Catheter System for Electrical Neuromodulation" and filed on May 22, 2014; PCT Patent Application No. PCT/US2015/179634, entitled "Catheter and Catheter System for Electrical Neuromodulation" and filed on May 21, 2015, U.S. Provisional Patent Application No. 62/047,270, entitled "Catheter and Electrode Systems for Electrical Neuromodulation" and filed on Sep. 8, 2014; PCT Patent Application No. PCT/US2015/047770, entitled "Catheter and Electrode Systems for Electrical Neuromodulation" and filed on Aug. 31, 2015; and U.S. patent application Ser. No. 14/085,311, entitled "Methods and Systems for Treating Acute Heart Failure by Neuromodulation" and filed on Nov. 20, 2013, where the contents of these applications are incorporated herein by reference in their entirety.

Several embodiments of the present disclosure provides methods that can be used to treat acute heart failure, also known as decompensated heart failure, by modulating the autonomic nervous system surrounding the pulmonary artery (e.g., the right pulmonary artery, the left pulmonary artery, the pulmonary trunk) in an effort to provide adjuvant cardiac therapy to the patient. The neuromodulation treatment can help by affecting heart contractility more than heart rate. In a preferred embodiment, the autonomic nervous system is modulated so as to collectively affect heart contractility more than heart rate. The autonomic nervous system can be impacted by electrical modulation that includes stimulating and/or inhibiting nerve fibers of the autonomic nervous system.

In some embodiments, systems other than intravascular catheters may be used in accordance with the methods described herein. For example, electrodes, sensors, and the like may be implanted during open heart surgery or without being routed through vasculature.

Several embodiments, as will be discussed more fully herein, may allow for the electrical neuromodulation of the heart of the patient that includes delivering one or more electrical pulses through a catheter positioned in a pulmonary artery of the heart of the patient, sensing from at least a first sensor positioned at a first location within the vasculature of the heart one or more heart activity properties (e.g., non-electrical heart activity properties) in response to the one or more electrical pulses, and adjusting a property of the one or more electrical pulses delivered through the catheter positioned in the pulmonary artery of the heart in response to the one or more heart activity properties in an effort to provide adjuvant cardiac therapy to the patient.

The catheter can include a plurality of electrodes, which are optionally inserted into the pulmonary trunk, and positioned such that the electrodes are, preferably, in contact with the posterior surface, the superior surface, and/or the inferior surface of the pulmonary artery. From such locations, electrical pulses can be delivered to or from the electrodes to selectively modulate the autonomic nervous system of the heart. For example, electrical pulses can be delivered to or from one or more of the electrodes to selectively modulate the autonomic cardiopulmonary nerves of the autonomic nervous system, which can modulate heart contractility more than heart rate. Preferably, the plurality of electrodes is positioned at a site along the posterior wall and/or superior wall of the pulmonary artery, for example the right pulmonary artery. From such a position in the pulmonary artery, one or more electrical pulses can be delivered through the electrodes and one or more heart activity properties (e.g., non-electrical heart activity properties) can be sensed. Based at least in part on these sensed heart activity properties, a property of the one or more electrical pulses delivered to or from the electrodes positioned in the pulmonary artery of the heart can be adjusted in an effort to positively influence heart contractility while reducing or minimizing the effect on heart rate and/or oxygen consumption. In certain embodiments, the effect on heart contractility is to increase heart contractility.

Figure 1B:
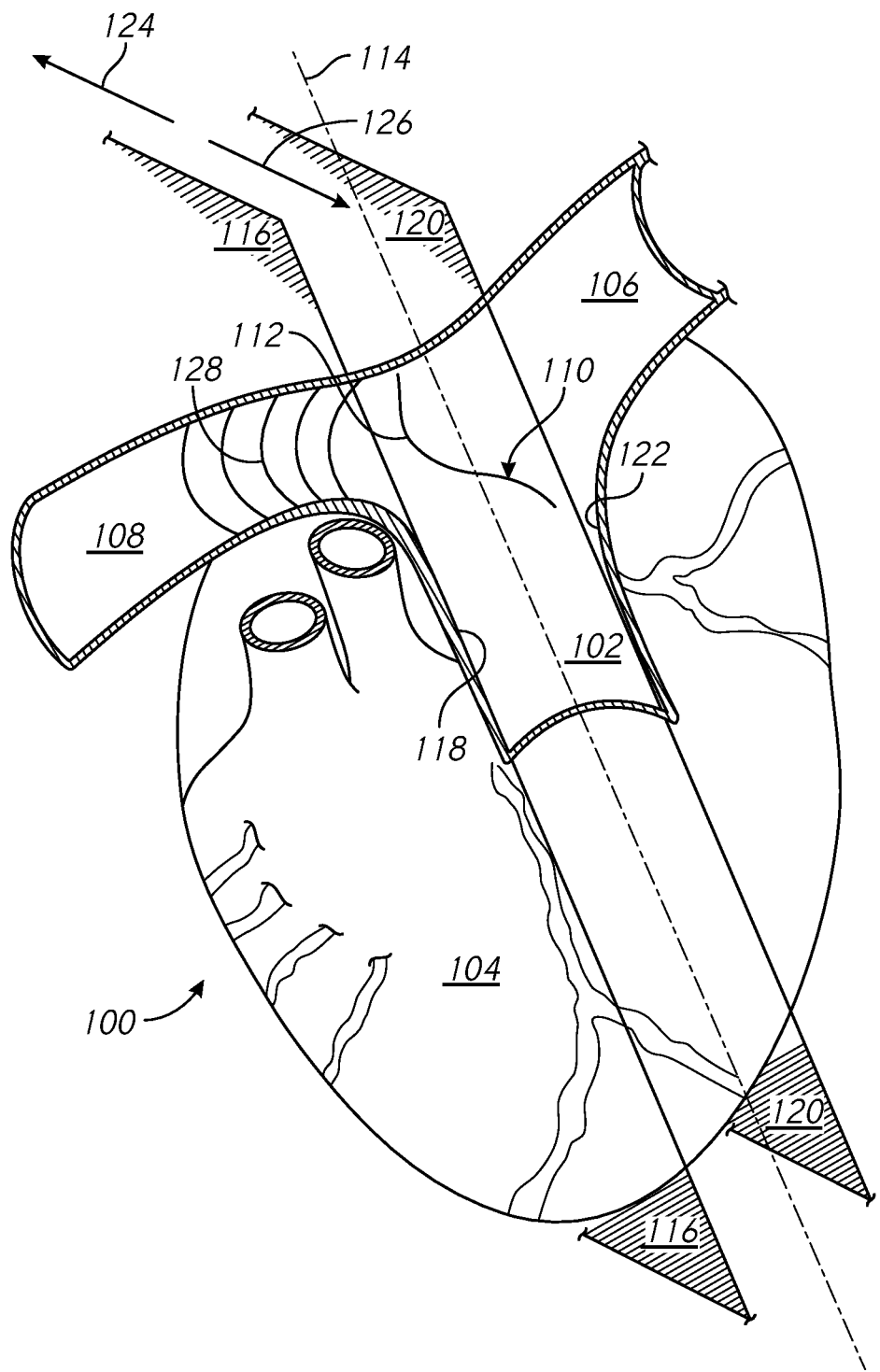
Figure 1C:
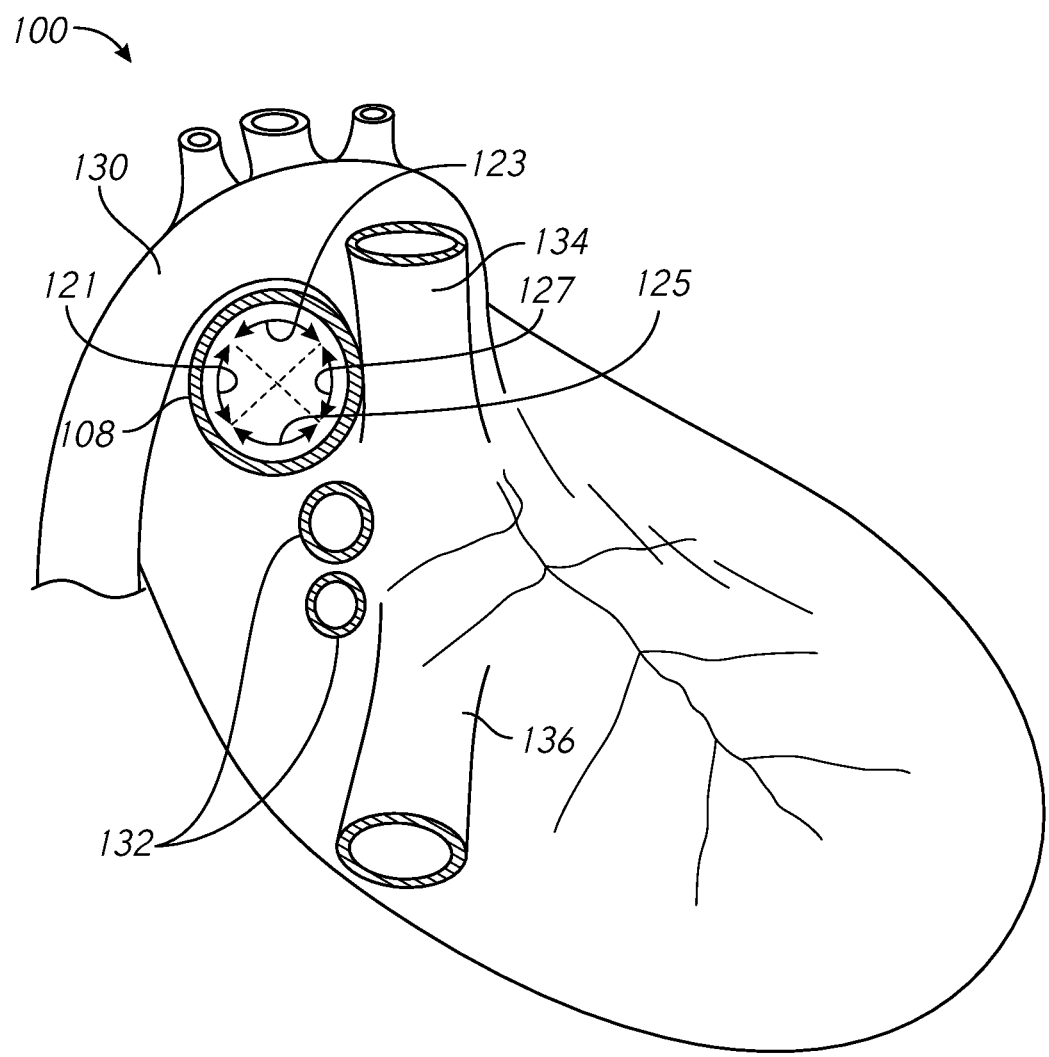

Referring now to FIGS. 1A through 1C, there is shown a schematic illustration of the human heart 100, where portions of the heart (e.g., the aorta, the superior vena cava, among other structures), including a portion of the pulmonary trunk 102, have been removed to allow for the details discussed herein to be shown. FIG. 1A provides a perspective view of the heart 100 as seen from the front of the patient (viewed in an anterior to posterior direction), while FIG. 1B provides a perspective view of the heart 100 as seen from the right side of the patient. As illustrated, the heart 100 includes the pulmonary trunk 102 that begins at the base of the right ventricle 104. In an adult, the pulmonary trunk 102 is a tubular structure approximately 3 centimeters (cm) in diameter and 5 cm in length. The pulmonary trunk 102 branches into the left pulmonary artery 106 and the right pulmonary artery 108 at a branch point 110. The left pulmonary artery 106 and the right pulmonary artery 108 serve to deliver de-oxygenated blood to each corresponding lung.

The branch point 110 includes a ridge 112 that extends from the posterior of the pulmonary trunk 102. As illustrated, the branch point 110, along with the ridge 112, provides a "Y" or "T" shaped structure that helps to define at least a portion of the left pulmonary artery 106 and the right pulmonary artery 108. For example, from the ridge 112, the branch point 110 of the pulmonary trunk 102 slopes in opposite directions. In a first direction, the pulmonary trunk 102 transitions into the left pulmonary artery 106, and in the second direction, opposite the first direction, the pulmonary trunk 102 transitions into the right pulmonary artery 108. The branch point 110 may not necessarily be aligned along a longitudinal center line 114 of the pulmonary trunk 102.

As illustrated in FIG. 1A, portions of the pulmonary artery 102 can be defined with a right lateral plane 116 that passes along a right luminal surface 118 of the pulmonary trunk 102, a left lateral plane 120 parallel with the right lateral plane 116, where the left lateral plane 120 passes along a left luminal surface 122 of the pulmonary artery 102. The right lateral plane 116 and the left lateral plane 120 extend in both a posterior direction 124 and anterior direction 126. As illustrated, the ridge 112 of the branch point 110 is located between the right lateral plane 116 and the left lateral plane 120. The branch point 110 is positioned between the right lateral plane 116 and the left lateral plane 120, where the branch point 110 can help to at least partially define the beginning of the left pulmonary artery 106 and the right pulmonary artery 108 of the heart 100. The distance between the right lateral plane 116 and the left lateral plane 120 is approximately the diameter of the pulmonary trunk 102 (e.g., about 3 cm).

As discussed herein, the present disclosure includes methods for electrical neuromodulation of the heart 100 of the patient. For example, as discussed herein, a catheter positioned in the pulmonary artery 102 of the patient can be used to deliver one or more electrical pulses to the heart 100. A first sensor, for example as discussed herein, positioned at a first location within the vasculature of the heart 100 senses one or more heart activity properties (e.g., non-electrical heart activity properties) in response to the one or more electrical pulses. Properties of the one or more electrical pulses delivered through the catheter positioned in the pulmonary artery 102 of the heart 100 can then be adjusted in response to the one or more heart activity properties in an effort to provide adjuvant cardiac therapy to the patient.

FIG. 1C provides an additional illustration the posterior surface 121, the superior surface 123, and the inferior surface 125 of the right pulmonary artery 108. As illustrated, the view of the heart 100 in FIG. 1C is from the right side of the heart 100. As illustrated, the posterior surface 121, the superior surface 123, and the inferior surface 125 account for approximately three quarters of the luminal perimeter of the right pulmonary artery 108, where the anterior surface 127 accounts for the remainder. FIG. 1C also illustrates the aorta 130, pulmonary veins 132, the superior vena cava (SVC) 134, and the inferior vena cava (IVC) 136.

Figure 2A:
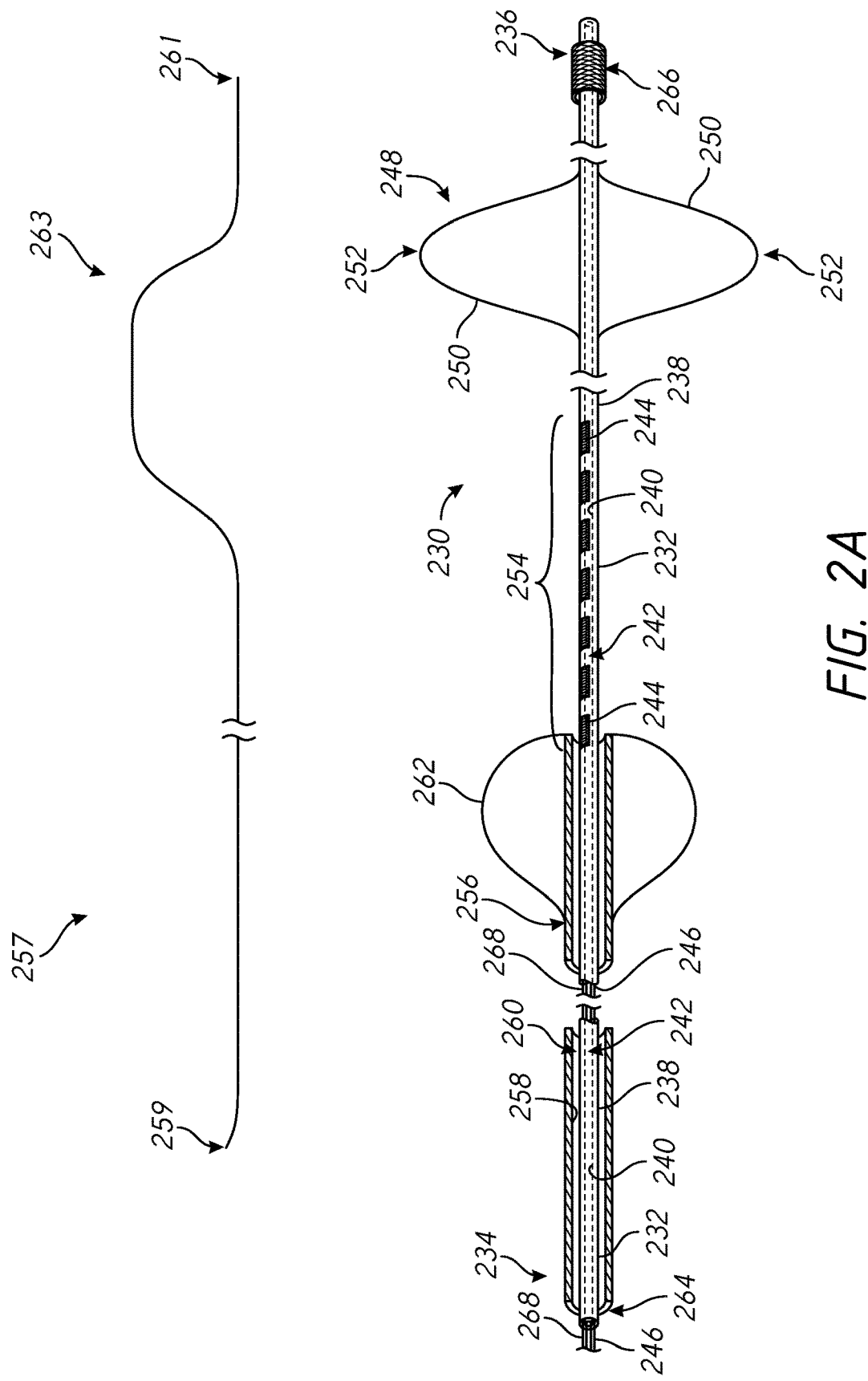
FIGS. 2A through 2C are side partial cross-sectional and perspective views of an example catheter that is suitable for performing the methods of the present disclosure.
Figure 2B:
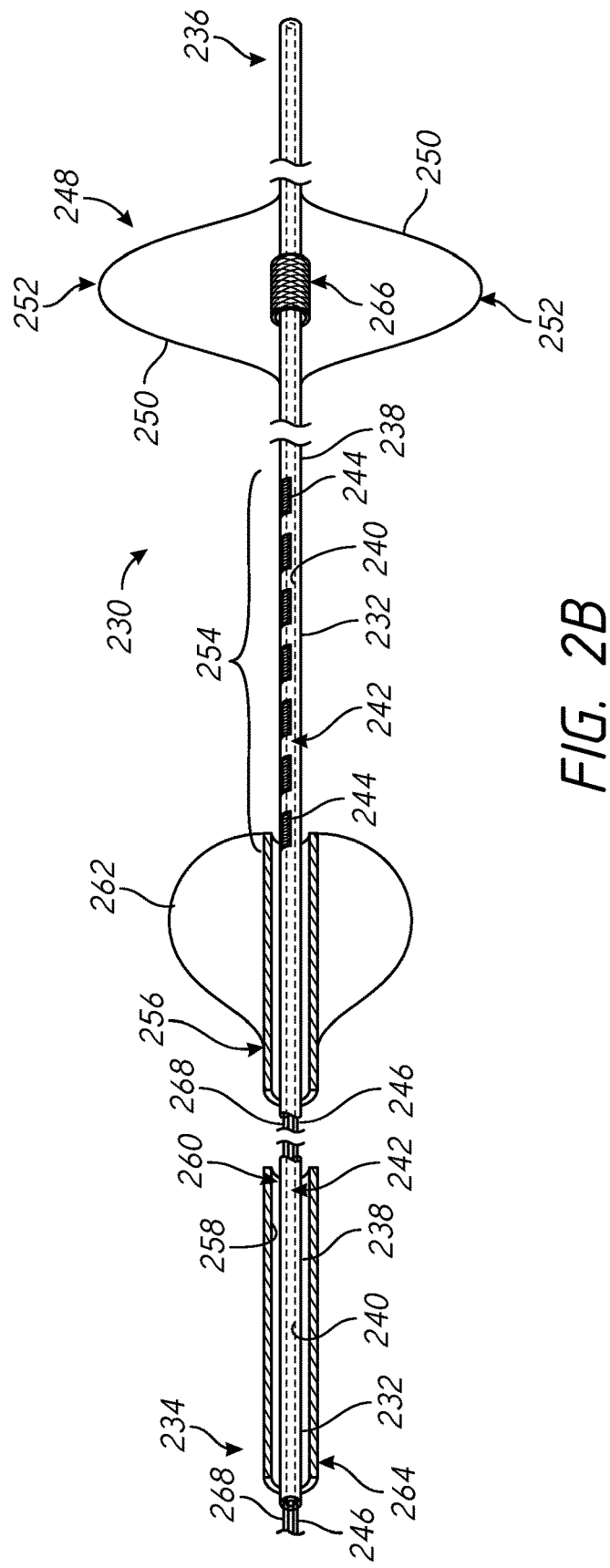
Figure 2C:
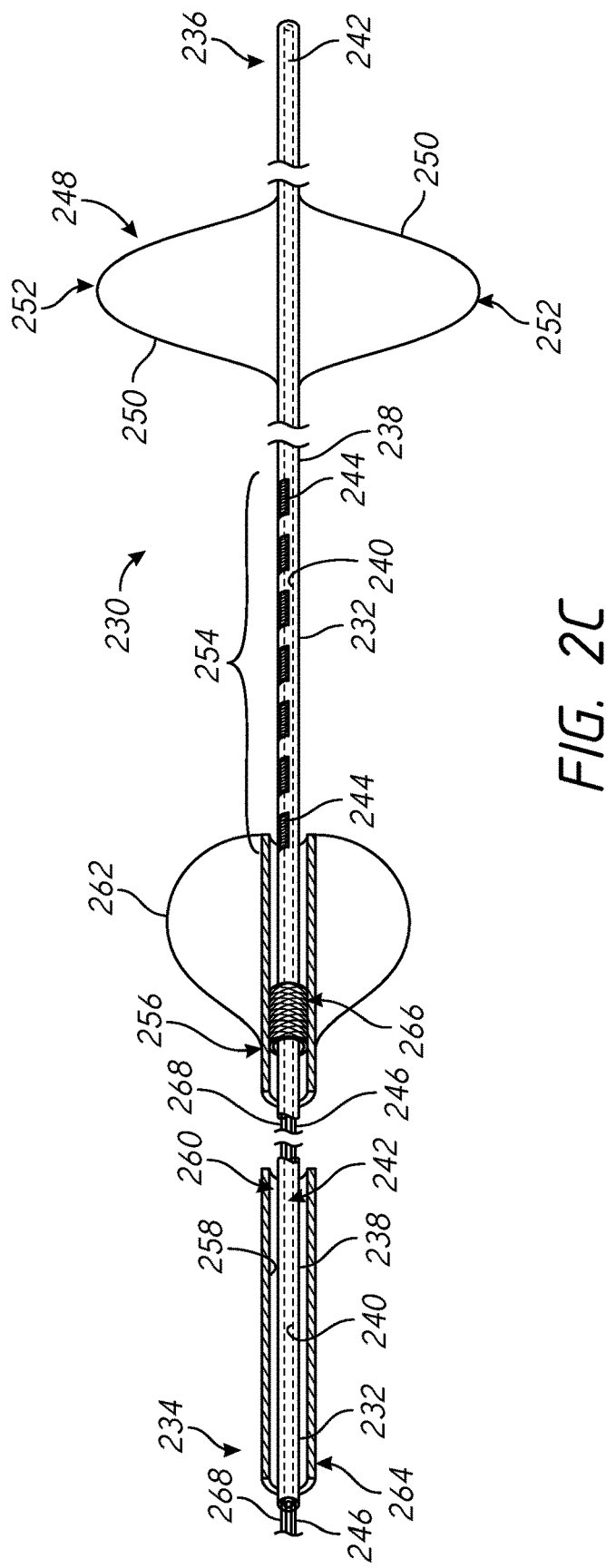

Referring now to FIGS. 2A through 2C, there are shown perspective views of an example catheter 230 that is suitable for performing certain methods of the present disclosure. The catheter 230 includes an elongate catheter body 232 having a proximal or first end 234 and a distal or second end 236. The elongate catheter body 232 also includes an outer or peripheral surface 238 and an interior surface 240 defining a lumen 242 (shown with a broken line) that extends between the first end 234 and the second end 236 of the elongate catheter body 232.

The catheter 230 further includes a plurality of electrodes 244 positioned along the peripheral surface 238 of the elongate catheter body 232. In some embodiments, the electrodes 244 are proximate to a distal end 236 of the catheter 230. Conductive elements 246 extend through the elongate body 232, where the conductive elements 246 can be used, as discussed herein, to conduct electrical pulses to combinations of the plurality of electrodes 244. Each of the plurality of electrodes 244 is coupled (e.g., electrically coupled) to a corresponding conductive element 246. The conductive elements 246 are electrically isolated from each other and extend through the elongate body 232 from each respective electrode 244 through the first end 234 of the elongate body 232. The conductive elements 246 terminate at a connector port, where each of the conductive elements 246 can be releasably coupled to a stimulation system. It is also possible that the conductive elements 246 are permanently coupled to the stimulation system (e.g., not releasably coupled). As discussed more fully herein, the stimulation system can be used to provide stimulation electrical pulses that are conducted through the conductive elements 246 and delivered across combinations of the plurality of electrodes 244. Other positions and configurations of electrodes are also possible, for example the electrodes described in the applications incorporated herein by reference (e.g., the electrodes on deployable filaments such as described in PCT Patent App. Nos. PCT/US2015/031960 and PCT/US2015/047770, the electrode matrix such as described in PCT Patent App. Nos. PCT/US2015/047770 and PCT/US2015/047780, and others).

The elongate body 232 may comprise (e.g., be at least partially formed of) an electrically insulating material. Examples of such insulating material can include, but are not limited to, medical grade polyurethanes, such as polyester-based polyurethanes, polyether-based polyurethanes, and polycarbonate-based polyurethanes; polyamides, polyamide block copolymers, polyolefins such as polyethylene (e.g., high density polyethylene), and polyimides, among others.

The catheter 230 optionally includes an anchor 248. The anchor 248 includes struts 250 that form an open framework, where the struts 250 extend laterally or radially outwardly from the elongate body 232 (e.g., from a peripheral surface 238 of the elongate body 232) to at least partially define a peripheral surface 252 configured to engage vascular tissue (e.g., configured to appose sidewalls forming the lumen of the right pulmonary artery and/or the left pulmonary artery). FIGS. 2A through 2C show the anchor 248 positioned between the second end 236 and the plurality of electrodes 244 of the elongate catheter body 232. It is also possible that the anchor 248 can be positioned between the plurality of electrodes 244 and the second end 236 of the elongate catheter body 232. In some embodiments, the anchor 248 can inhibit or prevent at least a portion of the catheter 230 (e.g., the portion 254, a portion comprising the electrodes 244) from extending into vasculature smaller than the expanded struts 250. For example, with reference to FIG. 3, the plurality of electrodes 344 can be proximal to the branch point 310 such that portions of the catheter 330 proximal to the anchor 348 do not extend into the two additional arteries 378. If the sensor 366 is distal to the anchor 348, interaction of the anchor 348 and the branch point 310 may ensure that the sensor 366 is in a pulmonary artery branch vessel 378.

The struts 250 can have a cross-sectional shape and dimension that allow for the struts 250 to provide a radial force sufficient to hold the catheter 230 at the implant location within the pulmonary artery under a variety of situations, as discussed herein. The struts 250 can be formed of a variety of materials, such as a metal, metal alloy, polymer, etc. Examples of such metals or metal alloys include surgical grade stainless steel, such as austenitic 316 stainless among others, and the nickel and titanium alloy known as Nitinol. Other metals and/or metal alloys, as are known or may be developed, can be used.

A portion 254 of the elongate catheter body 232, for example that includes one, some, none, or all the plurality of electrodes 244, can curve in a predefined radial direction (e.g., anterior, posterior, inferior, superior, and combinations thereof), for example when placed under longitudinal compression. To provide the curve in the portion 254, the elongate catheter body 232 can be pre-stressed and/or the wall can have thicknesses that allow for the elongate catheter body 232 to curve in the predefined radial direction, for example when placed under longitudinal compression. In addition, or alternatively, structures such as coils or a helix of wire having different turns per unit length, a hypotube having varying kerf spacing, etc. can be located in, around, and/or along the elongate catheter body 232 in the portion 254. One or more of these structures can be used to allow the longitudinal compression to create the curve in the predefined radial direction in the portion 254. To achieve the longitudinal compression, the anchor 248 can be deployed in the vasculature of the patient (e.g., in the pulmonary artery), where the anchor 248 provides a location or point of resistance against the longitudinal movement of the elongate body 232. As such, this allows a compressive force to be generated in the elongate catheter body 232 sufficient to cause the portion 254 of the elongate catheter body 232, for example along which the plurality of electrodes 244 are present, to curve in the predefined radial direction.

Figure 2D:
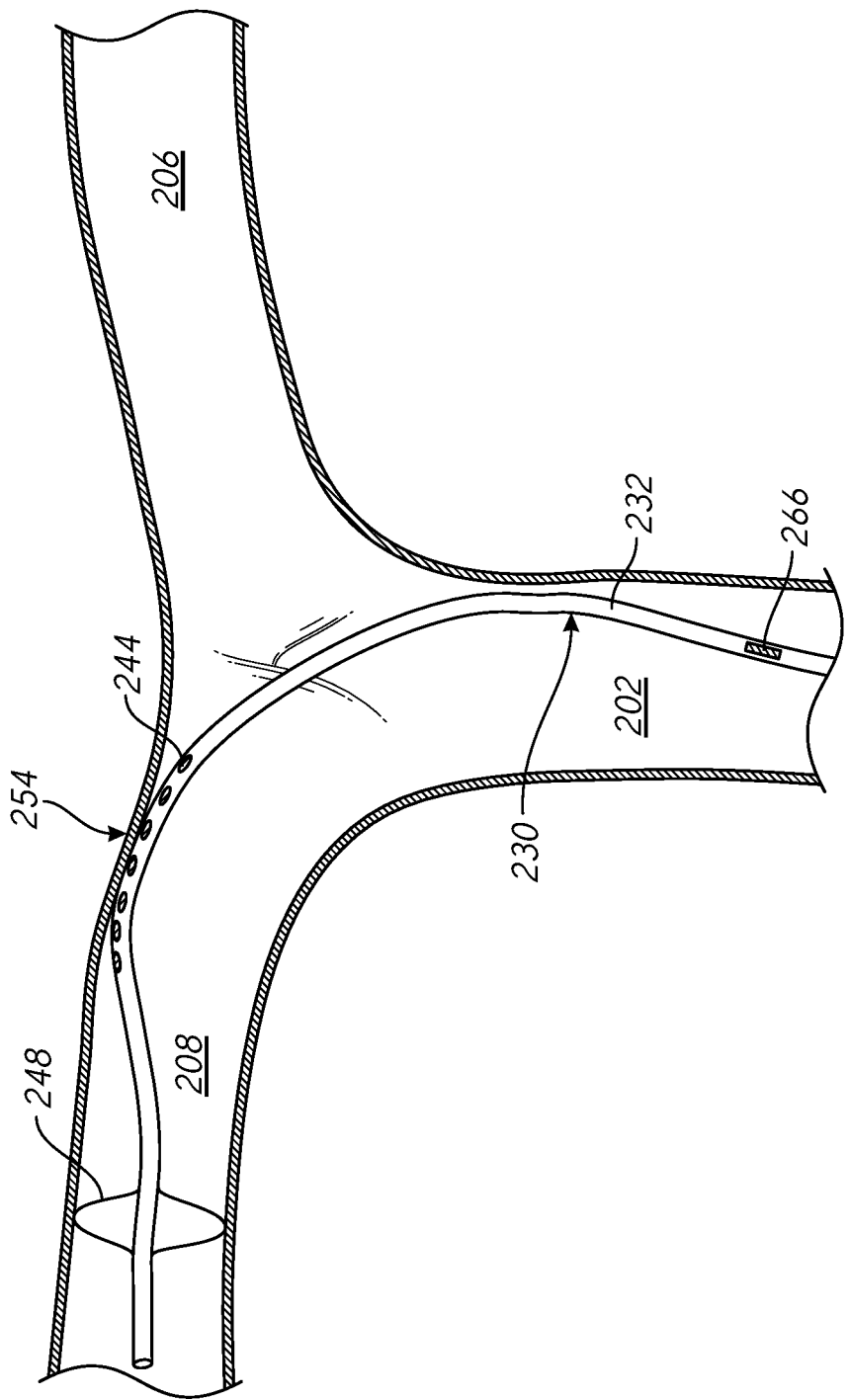
FIG. 2D illustrates the catheter of FIGS. 2A through 2C positioned in the right pulmonary artery of a heart.

FIG. 2D provides an illustration of the portion 254 of the elongate catheter body 232 curved in a predefined radial direction when placed under longitudinal compression. The catheter 230 illustrated in FIG. 2D is similar to the catheter 230 shown in FIG. 2A and is described herein, although other catheters having similar features can also be used. In the catheter 230 illustrated in FIG. 2D, the sensor 266 is proximal to the electrodes 244. When the electrodes are in the right pulmonary artery 208, the sensor 266 can be in the pulmonary trunk 202, for example. If the sensor 266 is more proximal, the sensor 266 can be in the right ventricle, the superior vena cava, etc. Positioning the sensor 266 proximal along the catheter 230 can allow the sensor 266 to be in a location different than the location of the electrode 244 without positioning the sensor 266 separate from positioning the electrode 244. As illustrated in FIG. 2D, the catheter 230 has been at least partially positioned within the main pulmonary artery 202 of a patient's heart 200, where the anchor 248 is located in the lumen of the right pulmonary artery 208. From this position, a longitudinal compressive force applied to the elongate catheter body 232 can cause the portion 254 of the elongate catheter body 232, along with at least some of the plurality of electrodes 244 in this embodiment, to curve in the predefined radial direction, superior in this embodiment. The curvature allows the plurality of electrodes 244 to extend towards and/or touch the luminal surface of the main and/or right pulmonary artery. Preferably, the plurality of electrodes 244 are brought into position and/or contact with the luminal surface of the main and/or right pulmonary artery.

In some embodiments, the elongate catheter body 232 of the catheter 230 can use the lumen 242 that extends from the first end 234 towards the second end 236 to provide a curve in a predefined radial direction. For example, the catheter 230 can include a shaping wire 257 having a first end 259 and a second end 261, as illustrated in FIG. 2A. The shaping wire 257 can be bent and retain a desired shape that, upon insertion into the lumen 242, can at least partially provide the catheter 230 with a curve. The lumen 242 has a size (e.g., a diameter) sufficient to allow the shaping wire 257 to pass through the lumen 242 with the second end 261 of the shaping wire 257 proximate to the second end 236 of the elongate catheter body 232 so that the bent portion 263 of the shaping wire 257 imparts a curve into the portion 254 of the elongate catheter body 232, allowing the plurality of electrodes 244 to extend towards and/or touch the luminal surface of the main pulmonary artery. In some embodiments the shaping wire 257 can complement the portion 254. In some embodiments, the shaping wire 257 can be used in place of the portion 254 (e.g., if the catheter 230 does not include the portion 254 or by not imparting the longitudinal compressive force). In some embodiments, the shaping wire 257 can be used to impart a curve that is contrary to the curve that the portion 254 would cause if a compressive force was applied. In some embodiments, the shaping wire 257 may be inserted into the lumen 242 in any rotational orientation such that a curve can be imparted in any desired radial direction, for example depending on the position of the anchor 248. The shaping wire 257 can allow formation of a curve even if the catheter 230 does not include an anchor 248, for example because the catheter body 232 can conform to the shape of the shaping wire regardless of whether the catheter 230 is anchored to the vasculature. In some embodiments, insertion of the shaping wire 257 into the lumen 242 imparts a curve to the portion 254 such that at least one of the electrodes 244 apposes a superior/posterior sidewall of the pulmonary artery.

In some embodiments, a neuromodulation system comprises a catheter 230 and a shaping wire 257. The catheter 230 comprises a catheter body 232, an electrode 244, and a sensor 266. The catheter body 232 comprises a proximal end 234, a distal end 236, a lumen 242 extending from the proximal end 234 towards the distal end 236 (e.g., at least distal to the electrode 244), and an outer surface 238. The electrode 244 is on the outer surface 238. The electrode 244 is configured to deliver an electrical signal to a pulmonary artery of a patient (e.g., to provide calibration and/or therapeutic stimulation to a nerve proximate the pulmonary artery).

The shaping wire 257 comprises a material that is configured to cause the catheter body 232 to bend. For example, the radial force of the shaping wire 257 may be greater than the forces that keep the catheter body 232 in a generally straight configuration. In some embodiments, the shaping wire 257 comprises a shape memory material (e.g., nitinol, chromium cobalt, copper aluminum nickel, etc.) or a resilient material (e.g., stainless steel, etc.). For example, the shaping wire 257 may be stressed to a straight wire in a proximal portion of the catheter 230, but in a portion of the catheter 230 to be bent, which may be, for example, weaker that the proximal portion of the catheter 230, the shaping wire 257 can revert to the unstressed curved shape within the catheter 230. In some embodiments in which the shaping wire 257 comprises a shape memory material, the shaping wire 257 may utilize thermal shape memory. For example, the shaping wire 257 may be in a substantially straight shape until cold or warm fluid (e.g., saline) causes reversion to the curved shape. In some such embodiments, the entire catheter 230 may be bendable by the shaping wire 257, but the temperature change is effected once the shaping wire 257 is in a desired longitudinal and/or radial position. In some embodiments, the entire catheter 230 may be bendable by the shaping wire 257. For example, the curve may propagate along the length of the catheter 230 until the curve is in a desired position.

The shaping wire 257 has a diameter or cross-sectional dimension less than the diameter or cross-sectional dimension of the lumen 242. For example, if the catheter body 232 is 20 French (Fr) (approx. 6.67 millimeters (mm)), the lumen 242 may be 18 Fr (approx. 6 mm) and the shaping wire 257 may be 16 Fr (approx. 5.33 mm). The shaping wire 257 may be, for example 1 Fr less than the lumen 242 (e.g., for more radial force than if 2 Fr less) or 2 Fr less than the lumen 242 (e.g., for less friction during navigation than if 1 Fr less). The shaping wire 257 may be, for example 2 Fr less than the catheter body 232 (e.g., if the lumen 242 is 1 Fr less than the catheter body 232) or 4 Fr less than the catheter body 232 (e.g., providing flexibility for the size of the lumen 242 to be 1 or 2 Fr less than the catheter body). Shaping wire sizes other than on a French catheter scale are also possible (e.g., having a diameter less than a diameter of the lumen 242 by about 0.05 mm, 0.1 mm, by about 0.2 mm, by about 0.25 mm, by about 0.5 mm, ranges between such values etc.).

The sensor 266 is on the outer surface 238. The sensor 266 is configured to sense a heart activity property (e.g., a non-electrical heart activity property such as a pressure property, an acceleration property, an acoustic property, a temperature, and a blood chemistry property) from a location within in vasculature of the patient. The location may be different than the pulmonary artery in which the electrode 244 is positioned. For example, if the electrode 244 is in the right pulmonary artery, the location of the sensor 266 may be in the pulmonary trunk, a pulmonary artery branch vessel, the right ventricle, the ventricular septal wall, the right atrium, the septal wall of the right atrium, the superior vena cava, the inferior vena cava, the left pulmonary artery, the coronary sinus, etc. The shaping wire 257 is configured to be positioned in the lumen 242 of the catheter body 232. The shaping wire comprising a bent portion 263. For example, from a proximal end 259 to a distal end 261, the shaping wire 257 may be substantially straight in a substantially straight portion, then have a bent portion 263 extending away from a longitudinal axis of the straight portion. The bent portion 263 may include one bend or a plurality of bends (e.g., two bends (as illustrated in FIG. 2A), three bends, or more bends). The shaping wire 257 may optionally comprise another substantially straight portion after the bent portion, which may have a longitudinal axis that is substantially aligned with the longitudinal axis of the proximal straight portion. When the shaping wire 257 is inserted in the lumen 242 of the catheter body 232, the catheter body 232 comprises a curved portion 254 corresponding to the bent portion 263 of the shaping wire 257. For example, the catheter body 232, or the portion 254, may comprise a material that can be bent due to pressure or stress applied to the lumen 242 or interior surface 240 of the catheter body 232. In some embodiments, insertion of the shaping wire 257 into the lumen 242 imparts a curve to the portion 254 such that at least one of the electrodes 244 apposes a superior/posterior sidewall of the pulmonary artery.

FIGS. 2A through 2C further illustrate an example delivery catheter 256 that can be used in conjunction with the catheter 230. The delivery catheter 256 can be a Swan-Ganz type pulmonary artery catheter, as are known, that includes a surface 258 defining a lumen 260 sized sufficiently to receive, store, and deploy the catheter 230. As illustrated, the delivery catheter 256 includes a reversibly inflatable balloon 262 in fluid communication with a balloon inflation lumen that extends from a proximal or first end 264 of the delivery catheter 256 (e.g., where the inflation lumen can be to an inflation fluid source) to the interior volume of the reversibly inflatable balloon 262.

The catheter 230 also includes a first sensor 266. As illustrated in FIGS. 2A through 2C, the first sensor 266 can be positioned at a number of different locations along the catheter 230. In FIG. 2A, the first sensor 266 is positioned on the elongate catheter body 232 distal to the anchor 248. A sensor 266 that is proximate to the distal end 236 of the catheter 230 may also or alternatively be useful for navigation of the catheter 230, for example to determine an anatomical location during floating a balloon such as with a Swan-Ganz catheter. In FIG. 2B, the first sensor 266 is positioned on or between one of the struts 250 of the anchor. In FIG. 2C, the first sensor 266 is positioned proximal to both the anchor 248 and the plurality of electrodes 244. In FIG. 2D, the first sensor 266 is positioned proximal enough that the first sensor 266 can be in a location of the vasculature different than the electrodes 244. In some embodiments, the catheter 230 comprises a plurality of sensors 266 at more than one of the positions illustrated in FIGS. 2A through 2C and/or other positions.

The catheter 230 further includes a sensor conductor 268. The first sensor 266 is coupled to the sensor conductor 268 and is isolated from the conductive elements 246 and electrodes 244. The coupling may be electrical, optical, pressure, etc. The sensor conductor 268 extends through the elongate body 232 from the first sensor 266 through the first end 234 of the elongate body 232. The sensor conductor 268 terminates at a connector port that can be used, for example, to releasably couple the first sensor 266 to the stimulation system, as discussed herein.

The first sensor 266 can be used to sense one or more activity property (e.g., electrical and/or non-electrical heart activity properties). In some embodiments, the property can be measured in response to one or more electrical pulses delivered using the plurality of electrodes 244. Examples of non-electrical heart activity properties include, but are not limited to, one or more of a pressure property, an acceleration property, an acoustic property, a temperature, and a blood chemistry property measured from within the vasculature of the heart. As appreciated, two or more of the non-electrical heart activity properties can be measured by using more than one sensor on the catheter 230.

For use in detecting a pressure property, the first sensor 266 can be a pressure sensing transducer, for example such as disclosed in U.S. Pat. No. 5,564,434 (e.g., configured to detect changes in blood pressure, atmospheric pressure, and/or blood temperature and to provide modulated pressure and/or temperature related signals), incorporated by reference herein in its entirety. For use in detecting an acceleration property, the first sensor 266 can be an acceleration sensor, for example such as disclosed in U.S. Patent Pub. No. 2004/0172079 to Chinchoy (e.g., configured to generate a signal proportional to acceleration of a heart muscle or wall such as a coronary sinus wall, septal wall, or ventricle wall) or U.S. Pat. No. 7,092,759 to Nehls et al. (e.g., configured to generate a signal proportional to acceleration, velocity, and/or displacement of a heart muscle or wall such as a coronary sinus wall, septal wall, or ventricle wall), each of which is incorporated by reference herein in its entirety. For use in detecting an acoustic property, the first sensor 266 can be a piezoelectric transducer (e.g., a microphone) or a blood flow sensor, for example such as disclosed in U.S. Pat. No. 6,754,532 (e.g., configured to measure a velocity of blood to estimate blood flow volume), which is incorporated by reference herein in its entirety. For use in detecting a temperature, the first sensor 266 can be a temperature sensor, for example such as disclosed in U.S. Pat. No. 5,336,244 (e.g., configured to detect variations in blood temperature and/or oxygen concentration indicative of the mechanical pumping action of the heart) and/or U.S. Patent Pub. No. 2011/0160790 (e.g., configured to sense temperature and to produce a temperature signal), each of which is incorporated by reference herein in its entirety. For use in detecting a blood chemistry properties, the first sensor 266 can be an oxygen sensor or a glucose sensor, for example such as disclosed in U.S. Pat. No. 5,213,098 (e.g., configured to sense blood oxygen saturation levels that vary with cardiac muscle oxygen uptake) and/or U.S. Patent Pub. No. 2011/0160790 (e.g., configured to measure oxygen and/or glucose concentration in blood and to produce an oxygen and/or glucose signal), each of which is incorporated by reference herein in its entirety. Other types of sensors can also be used for the first sensor 266 and other sensors described herein.

The catheter 230 shown in FIGS. 2A through 2C can be positioned in the right pulmonary artery, the left pulmonary artery, or the pulmonary trunk of the patient, as described herein. To accomplish this, the delivery catheter 256 with the catheter 230 housed therein can be introduced into the vasculature through a percutaneous incision, and guided to the right ventricle using known techniques. For example, the delivery catheter 256 can be inserted into the vasculature via a peripheral vein of the neck or chest (e.g., as with a Swan-Ganz catheter). Changes in a patient's electrocardiography and/or pressure signals from the vasculature can be used to guide and locate the pulmonary artery catheter within the patient's heart. Once in the proper location, a guide wire can be introduced into the patient via the pulmonary artery guide catheter, where the guide wire is advanced into the desired pulmonary artery (e.g., the right pulmonary artery). The delivery catheter 256 with the catheter 230 housed therein can be advanced over the guide wire so as to position the catheter 230 in the desired pulmonary artery of the patient (e.g., the right pulmonary artery or the left pulmonary artery), as described herein. Various imaging modalities can be used in positioning the guide wire of the present disclosure in the pulmonary artery of the patient. Such imaging modalities include, but are not limited to, fluoroscopy, ultrasound, electromagnetic, and electropotential modalities.

When the catheter 230 is positioned in the right pulmonary artery or the left pulmonary artery and the sensor 266 is configured to be proximal to the electrodes 244, a distance between the electrodes 244 (e.g., from the proximal-most electrode 244) and the sensor 266 may be between about 1 cm and about 5 cm (e.g., about 1 cm, about 2 cm, about 3 cm, about 4 cm, about 5 cm, ranges between such values, etc.), in which case the sensor 266 can reside in the pulmonary trunk, between about 8 cm and about 20 cm (e.g., about 8 cm, about 9 cm, about 10 cm, about 11 cm, about 12 cm, about 13 cm, about 14 cm, about 16 cm, about 18 cm, about 20 cm, ranges between such values, etc.), in which case the sensor 266 can reside in the right ventricle, between about 16 cm and about 27 cm (e.g., about 16 cm, about 17 cm, about 18 cm, about 19 cm, about 20 cm, about 21 cm, about 22 cm, about 23 cm, about 25 cm, about 27 cm, ranges between such values, etc.), in which case the sensor 266 can reside in the right atrium, or between about 21 cm and about 33 cm (e.g., about 21 cm, about 23 cm, about 25 cm, about 26 cm, about 27 cm, about 28 cm, about 29 cm, about 30 cm, about 31 cm, about 32 cm, about 33 cm, ranges between such values, etc.), in which case the sensor 266 can reside in the superior vena cava.

When the catheter 230 is positioned in the pulmonary trunk and the sensor 266 is configured to be distal to the electrodes 244, a distance between the electrodes 244 (e.g., from the distal-most electrode 244) and the sensor 266 may be between about 1 cm and about 5 cm (e.g., about 1 cm, about 2 cm, about 3 cm, about 4 cm, about 5 cm, ranges between such values, etc.), in which case the sensor 266 can reside in the right pulmonary artery or the left pulmonary artery. When the catheter 230 is positioned in the pulmonary trunk and the sensor 266 is configured to be proximal to the electrodes 244, a distance between the electrodes 244 (e.g., from the proximal-most electrode 244) and the sensor 266 may be between about 3 cm and about 19 cm (e.g., about 3 cm, about 5 cm, about 6 cm, about 7 cm, about 8 cm, about 9 cm, about 10 cm, about 12 cm, about 15 cm, about 19 cm, ranges between such values, etc.), in which case the sensor 266 can reside in the right ventricle, between about 11 cm and about 26 cm (e.g., about 11 cm, about 13 cm, about 15 cm, about 16 cm, about 17 cm, about 18 cm, about 19 cm, about 20 cm, about 22 cm, about 24 cm, about 26 cm, ranges between such values, etc.), in which case the sensor 266 can reside in the right atrium, or between about 16 cm and about 32 cm (e.g., about 16 cm, about 18 cm, about 20 cm, about 22 cm, about 24 cm, about 25 cm, about 26 cm, about 27 cm, about 28 cm, about 30 cm, about 32 cm, ranges between such values, etc.), in which case the sensor 266 can reside in the superior vena cava.

Figure 3:
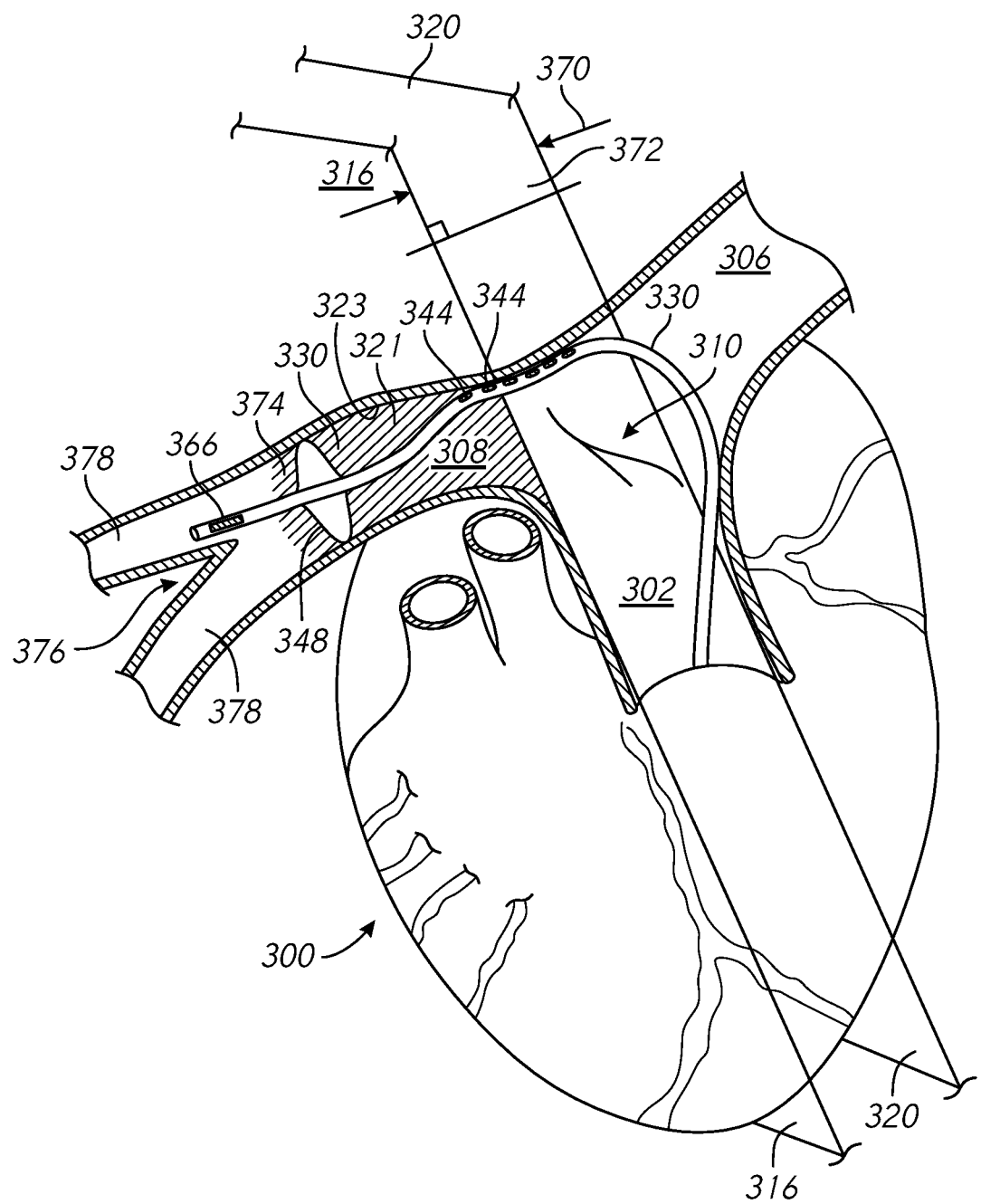
FIG. 3 is partial cross-sectional and perspective view of an example catheter positioned in a heart of a patient.

FIG. 3 provides a perspective view of the catheter 330 positioned in the heart 300 of the patient, where one or more of the plurality of electrodes 344 are contacting the posterior 321 and/or superior surface 323 of the right pulmonary artery 308 (e.g., at a position that is superior to the branch point 310). FIG. 3 further illustrates the embodiment in which the first sensor 366 is positioned distal from the anchor 348. As illustrated, the pulmonary trunk 302 has a diameter 370 taken across a plane 372 substantially perpendicular to both the left lateral plane 320 and the right lateral plane 316. In a preferred embodiment, the plurality of electrodes 344 of the catheter 330 is positioned in an area 374 that extends distally no more than about three times the diameter 370 of the pulmonary trunk 302 to the right of the branch point 310. This area 374 is shown with cross-hatching in FIG. 3.

The right pulmonary artery 308 can also include a branch point 376 that divides the right pulmonary artery 308 into at least two additional arteries 378 that are distal to the branch point 310 defining the left pulmonary artery 306 and the right pulmonary artery 308. As illustrated in FIG. 3, the plurality of electrodes 344 can be positioned between the branch point 310 defining the left pulmonary artery 306 and the right pulmonary artery 308 and the branch point 376 that divides the right pulmonary artery 308 into at least two additional arteries 378. In other words, the plurality of electrodes 344 of the catheter 330 could be positioned so as to contact the posterior 321 and/or superior surface 323 of the right pulmonary artery 308 up to an including the branch point 376.

Once positioned in a pulmonary artery of the heart of the patient (e.g., the right pulmonary artery 308 as illustrated in FIG. 3, the left pulmonary artery 306, and/or the pulmonary trunk 302), one or more therapeutic and/or calibrating electrical pulses can be delivered through the plurality of electrodes 344 of the catheter 330. One or more heart activity properties in response to the one or more electrical pulses are sensed from at least the first sensor 366 positioned at a first location within the vasculature of the heart 300.

The catheter 230, 330 may be permanently or reversibly implantable into the vasculature. For example, the catheter 230, 330 may be retracted from the vasculature (e.g., after removing the anchor 248, 348) after a duration. The duration may be determined based at least partially on a set duration (e.g., a certain number of hours or days (e.g., 12 hours, 18 hours, 24 hours, 2 days, 3 days, 4 days, 5 days, 6 days, etc.)). The duration may be determined based at least partially on a response of a patient (e.g., retracted when the patient has improved in an aspect by a certain amount or is deemed ready to have the catheter 230, 330 removed).

Figure 4:
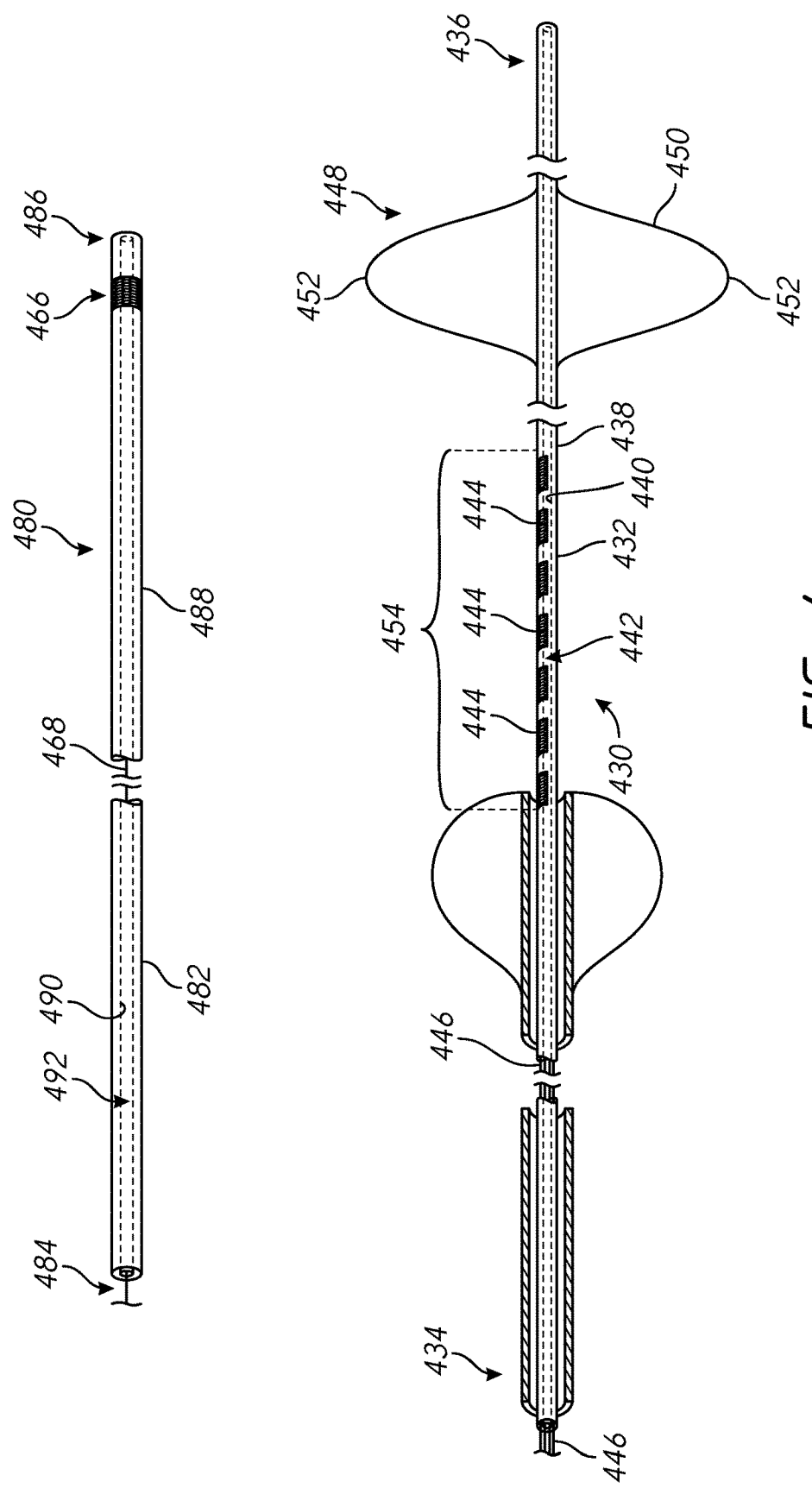
FIG. 4 is a side partial cross-sectional and perspective view of an example first catheter and an example second catheter that are suitable for performing the methods of the present disclosure.

FIG. 4 illustrates an example catheter 430 and a separate first sensor 466 useful for the methods of the present disclosure. Similar to the catheter 230, the catheter 430 includes an elongate catheter body 432 having a proximal or first end 434 and a distal or second end 436, a peripheral surface 438 and an interior surface 440 defining a lumen 442 (shown with a broken line) that extends between the first end 434 and the second end 436 of the elongate catheter body 432. The catheter 430 further includes a plurality of electrodes 444 positioned along the peripheral surface 438 of the elongate catheter body 432, and conductive elements 446 extending through the elongate body 432 between the plurality of electrodes 444 and the first end 434, as discussed herein. The catheter 430 further includes an anchor 448 comprising struts 450 that provide a peripheral surface 452 that can engage vascular tissue (e.g., the lumen of either the right pulmonary artery or the left pulmonary artery).

The catheter 430 further includes a portion 454 of the elongate catheter body 432, for example including the plurality of electrodes 444, where the portion 454 can curve in a predefined radial direction when placed under longitudinal compression, as discussed herein. The elongate catheter body 432 of the catheter 430 can also or alternatively include a lumen 442 that can receive a shaping wire, as discussed herein.

In contrast to the catheter illustrated in FIGS. 2A through 2D, however, the catheter 430 does not include a first sensor. Rather, a second catheter 480 includes a first sensor 466. As illustrated in FIG. 4, the second catheter 480 includes an elongate catheter body 482 having a first end 484 and a second end 486, a peripheral surface 488 and an interior surface 490 defining a lumen 492 (shown with a broken line) that extends between the first end 484 and the second end 486 of the elongate catheter body 482, where the lumen 492 can receive a guide wire for help in positioning the second catheter 480 in the vasculature of the heart. The second catheter 480 further includes a first sensor 466, as discussed herein, on the elongate catheter body 482 and a sensor conductor 468 that extends through the elongate catheter body 482 to terminate at a connector port that can be used, for example, to releasably couple the first sensor 466 to the stimulation system, as discussed herein.

As the first sensor 466 is included on the second catheter 480, the first sensor 466 can be positioned in a location within the vasculature of the patient that is different than the first location in which the catheter 430 is positioned. For example, the catheter 430 can be positioned with the plurality of electrodes 444 positioned in the right pulmonary artery, as discussed herein, while the first sensor 466 is positioned in the left pulmonary artery. In this way, one or more electrical pulses can be delivered through the catheter 430 positioned in the right pulmonary artery of the heart that does not contain the first sensor 466. In some embodiments, when the catheter 430 is positioned with the plurality of electrodes 444 positioned in the left pulmonary artery, the first sensor 466 can be positioned in the right pulmonary artery. In this way, one or more electrical pulses can be delivered through the catheter 430 positioned in the left pulmonary artery of the heart that does not contain the first sensor 466.

In some embodiments, the catheter 430 can be positioned with the plurality of electrodes 444 positioned in either one of the left pulmonary artery or the right pulmonary artery, and the first sensor 466 on the second catheter 480 can be positioned in the right ventricle of the heart. The first sensor 466 on the second catheter 480 can also be positioned in the right atrium of the heart.

In some embodiments, the first sensor 466 on the second catheter 480 can also be positioned on the septal wall of the right atrium or the ventricular septal wall of the heart. The elongate catheter body 482 of the second catheter 480 can include a positive fixation structure (e.g., a helical screw) that helps to secure the elongate catheter body 482 and the first sensor 466 to the septal wall of the right atrium of the heart.

In some embodiments the first sensor 466 on the second catheter 480 can be positioned in a superior vena cava of the heart. In some embodiments, the first sensor 466 on the second catheter 480 can be positioned in an inferior vena cava of the heart. In some embodiments, the first sensor 466 on the second catheter 480 can be positioned in a coronary sinus of the heart. In a preferred embodiment, when the first sensor 466 is positioned in the coronary sinus of the heart, the first sensor 466 is used to sense at least one of a temperature and a blood oxygen level.

One or more cardiac properties can also or alternatively be sensed from a skin surface of the patient. An example of such a cardiac property includes an electrocardiogram property, where the electrical activity of the heart can be sensed using electrodes, as are known, attached to the surface of the patient's skin. Another example of such a cardiac property can include a doppler echocardiogram, which can be used to determine the speed and direction of the blood flow. Acoustic signals sensed from the skin surface of the patient may also be used as the cardiac property. The properties of the one or more electrical pulses delivered through the catheter positioned in the pulmonary artery of the heart can then be adjusted, as discussed herein, in response to the one or more heart activity properties measured intravascularly and/or the one or more cardiac properties from the skin surface of the patient.

In some embodiments, a second sensor located at a second location within the vasculature of the heart can be used, in addition to the first sensor, to sense one or more heart activity properties, as discussed herein, for example in response to the one or more electrical pulses. The second location is different than the first location. For example, the first location may be the left pulmonary artery and the second location may be the right pulmonary artery; the first location may be the left pulmonary artery and the second location may be the pulmonary trunk; the first location may be the left pulmonary artery and the second location may be the right ventricle; the first location may be the left pulmonary artery and the second location may be the right atrium; the first location may be the left pulmonary artery and the second location may be the septal wall of the right atrium; the first location may be the left pulmonary artery and the second location may be the ventricular septal wall; the first location may be the left pulmonary artery and the second location may be the superior vena cava; the first location may be the left pulmonary artery and the second location may be the inferior vena cava; the first location may be the left pulmonary artery and the second location may be the coronary sinus; and other permutations of these locations.

In some embodiments, the second sensor is the sensor 466 of the second catheter 480, and the first sensor is the sensor 266 of the catheter 230. In some embodiments the first sensor and the second sensor can be located on the same catheter (e.g., the catheter 230, the catheter 480). For example, both the first sensor and the second sensor can be located on the second catheter 480 for sensing at least two different heart activity properties. For another example, both the first sensor and the second sensor can be located on the catheter 230 for sensing at least two different heart activity properties. The properties of the one or more electrical pulses delivered through the catheter positioned in the pulmonary artery of the heart can be adjusted, as discussed herein, in response to the one or more heart activity properties received from the first sensor and the second sensor.

Neuromodulation of the heart according to the present disclosure can be accomplished by applying electrical pulses in and/or around the region of the pulmonary artery. For example, the neuromodulation of the present disclosure can apply the electrical pulses to the posterior, superior wall, and/or the inferior wall of the right pulmonary artery. Preferably, neuromodulation of the present disclosure includes applying the electrical pulses to the posterior and/or superior wall of the right pulmonary artery, although other positions in the right pulmonary artery, the left pulmonary artery, and the pulmonary trunk are also possible. The electrical pulses are thereby applied to the autonomic cardiopulmonary nerves surrounding the right pulmonary artery. These autonomic cardiopulmonary nerves can include the right autonomic cardiopulmonary nerves and the left autonomic cardiopulmonary nerves. The right autonomic cardiopulmonary nerves include the right dorsal medial cardiopulmonary nerve and the right dorsal lateral cardiopulmonary nerve. The left autonomic cardiopulmonary nerves include the left ventral cardiopulmonary nerve, the left dorsal medial cardiopulmonary nerve, the left dorsal lateral cardiopulmonary nerve, and the left stellate cardiopulmonary nerve. Stimulation of other nerves proximate to the right pulmonary artery is also possible.

With reference FIG. 3, one or more of the plurality of electrodes 344 of the catheter 330 can be contacting the posterior surface 321 of the right pulmonary artery 308. From this location, the electrical pulses delivered through one or more of the plurality of electrodes 344 may be better able to treat and/or provide therapy (including adjuvant therapy) to the patient experiencing a variety of cardiovascular medical conditions, such as acute heart failure. The electrical pulses can elicit responses from the autonomic nervous system that may help to modulate a patient's cardiac contractility. The electrical pulses applied by the methods described herein preferably affect heart contractility more than the heart rate, which can help to improve hemodynamic control while possibly and/or reducing or minimizing unwanted systemic effects.

A stimulation system is electrically coupled to the plurality of electrodes of the catheter via the conductive elements extending through the catheter. The stimulation system can be used to deliver the electrical pulses to the autonomic cardiopulmonary fibers surrounding the pulmonary artery (e.g., the right pulmonary artery). The stimulation system is used to operate and supply the electrical pulses to the plurality of electrodes of the catheter. The stimulation system controls the various properties of the electrical pulses delivered across the plurality of electrodes. Such properties include control of polarity (e.g., used as a cathode or an anode), pulsing mode (e.g., unipolar, bi-polar, biphasic, and/or multi-polar), a pulse width, an amplitude, a frequency, a phase, a voltage, a current, a duration, an inter-pulse interval, a dwell time, a sequence, a wavelength, and/or a waveform associated with the electrical pulses. The stimulation system may operate and supply the electrical pulses to different combinations and numbers of the plurality of electrodes, including a reference electrode. The stimulation system can be external to the patient's body or internal to the patient's body. When located outside the body, a professional can program the stimulation system and monitor its performance. When located within the patient, the housing of the stimulation system or an electrode incorporated in the housing can be used as a reference electrode for both sensing and unipolar pulsing mode.

Examples of non-electrical heart activity properties include, but are not limited to, a pressure property, an acceleration property, an acoustic property, a temperature, or a blood chemistry property. The non-electrical heart activity properties may be sensed by at least a first sensor positioned at a first location within the vasculature of the heart. In response to the one or more non-electrical heart activity properties, a property of the one or more electrical pulses delivered through the catheter positioned in the pulmonary artery of the heart can be adjusted. Examples of such adjustments include, but are not limited to, changing which electrode or electrodes of the plurality of electrodes on the catheter is/are used to deliver one or more electrical pulses. Adjustments can also be made to the properties of the electrical pulses, for example by changing at least one of an electrode polarity, a pulsing mode, a pulse width, an amplitude, a frequency, a phase, a voltage, a current, a duration, an inter-pulse interval, a duty cycle, a dwell time, a sequence, a wavelength, and a waveform of the one or more electrical pulses. It is possible to adjust combinations of electrodes used and the properties of the electrical pulses provided by the electrodes. Adjusting a property of the one or more electrical pulses can include moving the catheter to reposition electrodes of the catheter in the pulmonary artery of the heart. Combinations of these adjustments are also possible.

By way of example, the electrical pulses can have a voltage between about 0.1 microvolts (mV) and about 75 volts (V) (e.g., about 0.1 mV, about 0.5 mV, about 1 mV, about 10 mV, about 100 mV or about 0.1 V, about 1 V, about 10 V, about 20 V, about 30 V, about 40 V, about 50 V, about 60 V, about 75 V, ranges between such values, etc.). The electrical pulses can also have an amplitude between about 1 milliamps (mA) to about 40 mA (e.g., about 1 mA, about 2 mA, about 3 mA, about 4 mA, about 5 mA, about 10 mA, about 15 mA, about 20 mA, about 25 mA, about 30 mA, about 35 mA, about 40 mA, ranges between such values, etc.). The electrical pulses can be delivered at a frequency of between 1 Hertz (Hz) and about 10,000 Hz or 10 kilohertz (kHz) (e.g., about 1 Hz, about 2 Hz, about 10 Hz, about 25 Hz, about 50 Hz, about 75 Hz, about 100 Hz, about 150 Hz, about 200 Hz, about 250 Hz, about 500 Hz, about 1,000 Hz or 1 kHz, about 10 kHz, ranges between such values, etc.). The electrical pulses can have a pulse width between about 100 microseconds (μs) and about 100 milliseconds (ms) (e.g., about 100 μs, about 200 μs, about 500 μs, about 1,000 μs or 1 ms, about 10 ms, about 50 ms, about 100 ms, ranges between such values, etc.). For variation of duty cycle, or the duration that the electrical pulses are delivered versus the duration that electrical pulses are not delivered, the electrical pulses may be delivered for between about 250 ms and about 1 second (e.g., about 250 ms, about 300 ms, about 350 ms, about 400 ms, about 450 ms, about 500 ms, about 550 ms, about 600 ms, about 650 ms, about 700 ms, about 750 ms, about 800 ms, about 850 ms, about 900 ms, about 950 ms, ranges between such values, etc.), and thereafter not delivered for between about 1 second and about 10 minutes (e.g., about 1 second, about 5 seconds, about 10 seconds, about 15 seconds, about 30 seconds, about 45 seconds, about 1 minute, about 2 minutes, about 3 minutes, about 5 minutes, about 10 minutes, ranges between such values, etc.). An optimized duty cycle may, for example, reduce response time, increase battery life, patient comfort (reduce pain, cough, etc.), etc. The electrical pulses can also have a variety of waveforms, such as: square wave, biphasic square wave, sine wave, arbitrary defined waveforms that are electrically safe, efficacious, and feasible, and combinations thereof. The electrical pulses may be applied to multiple target sites via multiple electrodes at least partially simultaneously and/or sequentially.

The methods of the present disclosure can include assigning a hierarchy of electrode configurations from which to deliver the one or more electrical pulses. The hierarchy can include two or more predetermined patterns and/or combinations of the plurality of electrodes to use in delivering the one or more electrical pulses. For example, the one or more electrical pulses can be delivered using the hierarchy of electrode configurations. A heart activity property sensed in response to the one or more electrical pulses delivered using the hierarchy of electrode configurations can be analyzed. Such an analysis can include, for example, determining which of the hierarchy of electrode configurations provide the highest contractility or relative contractility of the patient's heart. Based on this analysis, an electrode configuration can be selected to use for delivering the one or more electrical pulses through the catheter positioned in the pulmonary artery of the patient's heart.

In some embodiments, a method can include assigning a hierarchy to one or more properties of the one or more electrical pulses delivered through the catheter positioned in the pulmonary artery of the heart. The hierarchy can include providing an order of which property (e.g., electrode polarity, pulsing mode, pulse width, amplitude, frequency, phase, voltage, current, duration, inter-pulse interval, duty cycle, dwell time, sequence, wavelength, or waveform of the one or more electrical pulses) is to be changed and by how much, and for a predetermined number of electrical pulses delivered to the patient's heart. The predetermined number of electrical pulses can be, for example, 10 to 100 electrical pulses at a given property of the hierarchy. The one or more heart activity properties can be recorded for the predetermined number of the one or more electrical pulses delivered to the patient's heart for a given property of the one or more electrical pulses. The one or more heart activity properties sensed in response to the one or more electrical pulses can then be analyzed. For example, the recorded properties for each set of predetermined numbers of pulses can be analyzed against other sets of recorded properties and/or against predetermined standards for a given heart activity properties and/or cardiac property (e.g., contractility). Based on this analysis, an electrode configuration can be selected to use for delivering the one or more electrical pulses through the catheter positioned in the pulmonary artery of the patient's heart. As a non-limiting example, a current of 1 mA can be applied to an electrode for 50 electrical pulses, followed by the application of a current of 10 mA to the electrode for 50 electrical pulses. The responses at 1 mA and 10 mA can be compared. If 10 mA works better, a current of 20 mA can be applied to the electrode for 50 electrical pulses, and the responses at 10 mA and 20 mA can be compared. If 10 mA works better, 10 mA may be selected as the current for the method. A wide variety of selection processes may be used, including but not limited to iterative methods (e.g., comprising making comparisons until a limit is found at which a difference is negligible) and brute force methods (e.g., measuring responses and selecting one magnitude after completion of all responses or until a certain value is achieved). This can be repeated for one or more additional properties according to the hierarchy (e.g., current followed by frequency). The selection process may be the same or different for each member of the hierarchy.

In some embodiments, a first electrical signal of a series of electrical signals is delivered (e.g., via a stimulation system such as the stimulation system 501) to an electrode in the pulmonary artery (e.g., the right pulmonary artery, the left pulmonary artery, the pulmonary trunk). After delivering the first electrical signal, a second electrical signal of the series of electrical signals is delivered (e.g., via the stimulation system) to the electrode. The second electrical signal differs from the first electrical signal by a magnitude of a first parameter of a plurality of parameters. For example, if the first parameter is current, the first electrical signal may have a voltage such as 1 mA and the second electrical signal may have a different voltage such as 2 mA, while each of the other parameters (e.g., polarity, pulse width, amplitude, frequency, voltage, duration, inter-pulse interval, dwell time, sequence, wavelength, and waveform) are the same.

Sensor data indicative of one or more non-electrical heart activity properties may be determined in response to delivering the series of electrical signals (e.g., via a sensor in the vasculature (e.g., as part of a same catheter that comprises the electrode, as part of a different catheter), via a sensor on a skin surface, combinations thereof, and the like)). Electrical parameters to use for therapeutic modulation may be selected based at least partially on the sensor data. For example, the selected electrical parameters may comprise a selected magnitude of the first parameter. A therapeutic neuromodulation signal may be delivered to the pulmonary artery using selected electrical parameters. The therapeutic neuromodulation signal may increase heart contractility (e.g., more than heart rate).

In some embodiments, a first series of electrical signals is delivered (e.g., via a stimulation system such as the stimulation system 501) to an electrode in the pulmonary artery (e.g., the right pulmonary artery, the left pulmonary artery, the pulmonary trunk). The first series comprises a first plurality of electrical signals. Each of the first plurality of electrical signals comprises a plurality of parameters (e.g., polarity, pulsing mode, pulse width, amplitude, frequency, phase, voltage, current, duration, inter-pulse interval, duty cycle, dwell time, sequence, wavelength, waveform, subsets thereof, or the like). Each of the first plurality of electrical signals of the first series only differs from one another by a magnitude of a first parameter of the plurality of parameters (e.g., one of polarity, pulsing mode, pulse width, amplitude, frequency, phase, voltage, current, duration, inter-pulse interval, duty cycle, dwell time, sequence, wavelength, and waveform changes in each of the first plurality of electrical signals). For example, if the first parameter is current, the first plurality of electrical signals of the first series may differ by having different currents such as 1 mA, 2 mA, 3 mA, 4 mA, etc., while each of the other parameters (e.g., polarity, pulsing mode, pulse width, amplitude, frequency, phase, voltage, duration, inter-pulse interval, duty cycle, dwell time, sequence, wavelength, and waveform) are the same.

After the first series of electrical signals is delivered to the electrode, a second series of electrical signals can be delivered (e.g., via the stimulation system) to the electrode. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters different than the first parameter (e.g., a different one of polarity, pulsing mode, pulse width, amplitude, frequency, phase, voltage, current, duration, inter-pulse interval, duty cycle, dwell time, sequence, wavelength, and waveform changes in each of the second plurality of electrical signals). For example, if the first parameter is current, the second parameter may be related to timing such as frequency or duty cycle, For example, in the case of frequency, the second plurality of electrical signals of the second series may differ by having different frequencies such as 1 Hz, 2 Hz, 3 Hz, 4 Hz, etc., while each of the other parameters (e.g., current, polarity, pulsing mode, pulse width, amplitude, phase, voltage, duration, inter-pulse interval, duty cycle, dwell time, sequence, wavelength, and waveform) are the same.

Sensor data indicative of one or more non-electrical heart activity properties may be determined in response to delivering the first series of electrical signals and the second series of electrical signals (e.g., via a sensor in the vasculature (e.g., as part of a same catheter that comprises the electrode, as part of a different catheter), via a sensor on a skin surface, combinations thereof, and the like)). Electrical parameters to use for therapeutic modulation may be selected based at least partially on the sensor data. For example, the selected electrical parameters may comprise a selected magnitude of the first parameter and a selected magnitude of the second parameter. A therapeutic neuromodulation signal may be delivered to the pulmonary artery using selected electrical parameters. The therapeutic neuromodulation signal may increase heart contractility (e.g., more than heart rate).

Other series of electrical signals may be delivered to the electrode, for example only differing from one another by a magnitude of a different parameter of the plurality of parameters than the first parameter and the second parameter. As many parameters as may be desired to have a selected value may be calibrated or optimized. An order of the parameters may be based on a hierarchy (e.g., first select a current, then select a frequency, etc.).

A calibration or optimization process may be performed once (e.g., when a catheter 230, 330 is initially positioned) or a plurality of times. For example, the process may be repeated periodically or after a certain duration (e.g., once per hour, per 2 hours, per 4 hours, per 6 hours, per 8 hours, per 12 hours, per 18 hours, per 24 hours, per 36 hours, per 2 days, per 60 hours, per 3 hours, etc.). In some implementations the process may be repeated upon detection of a change (e.g., by the sensor 266, 366, 466). For example, if a heart activity property changes by more than a certain percentage in a certain duration (e.g., ±10%, ±25%, ±50%, etc. in ≤1 minute, ≤2 minutes, ≤5 minutes, etc.), that may be indicative that the catheter and/or sensor changed position or that something else in the system or patient may have changed (e.g., patient condition, physiological status, other therapy regiments, etc.).

Suitable examples of a stimulation system for use with the catheter in the method of the present disclosure can be found in U.S. Provisional Patent Application No. 62/001,729, entitled "Catheter and Catheter System for Electrical Neuromodulation" and filed on May 22, 2014; PCT Patent Application No. PCT/US2015/179634, entitled "Catheter and Catheter System for Electrical Neuromodulation" and filed on May 21, 2015; U.S. Provisional Patent Application No. 62/047,270, entitled "Catheter and Electrode Systems for Electrical Neuromodulation" and filed on Sep. 8, 2014; PCT Patent Application No. PCT/US2015/047770, entitled "Catheter and Electrode Systems for Electrical Neuromodulation" and filed on Aug. 31, 2015; and U.S. patent application Ser. No. 14/085,311, entitled "Methods and Systems for Treating Acute Heart Failure by Neuromodulation" and filed on Nov. 20, 2013.

Figure 5:
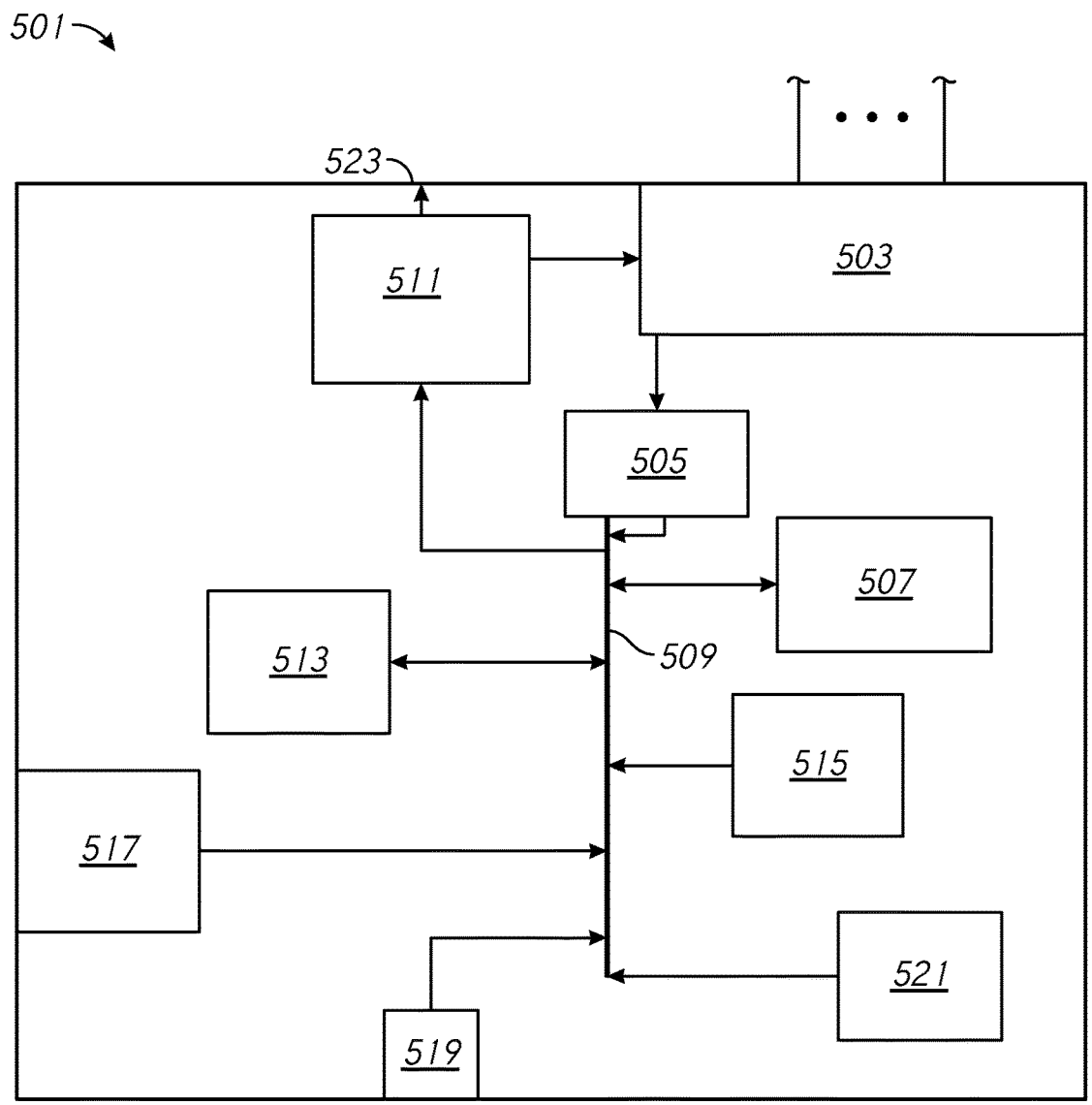
FIG. 5 is a block diagram of an example algorithm that can be used to determine action taken by a controller microprocessor in response to sensor input.

For example, FIG. 5 provides an illustration of the stimulation system similar to the stimulation system 11600 disclosed in U.S. Provisional Patent Application 62/001,729, entitled "Catheter and Catheter System for Electrical Neuromodulation" and filed on May 22, 2014, which is hereby incorporated by reference in its entirety, and more specifically from which FIG. 11 and page 41, line 5 to page 42, line 19 are incorporated herein by reference. As shown in FIG. 5, the stimulation system 501 includes an input/output connector 503 that can releasably join the conductive elements of the catheter, conductive elements of a second catheter, and/or sensors for sensing the one or more cardiac properties from the skin surface of the patient, as discussed herein. The conductive elements and/or sensors may be permanently coupled to the stimulation system (e.g., not releasably coupled).

The input/output connector 503 is connected to an analog to digital converter 505. The output of the analog to digital converter 505 is connected to a microprocessor 507 through a peripheral bus 509 including, for example, address, data, and control lines. The microprocessor 507 can process the sensor data, when present, in different ways depending on the type of sensor in use. The microprocessor 507 can also control, as discussed herein, the pulse control output generator 511 that delivers the electrical pulses to the one or more electrodes via the input/output connector 503 and/or housing 523.

The properties of the electrical pulses can be controlled and adjusted, if desired, by instructions programmed in a memory 513 and executed by a programmable pulse generator 515. The memory 513 may comprise a non-transitory computer-readable medium. The memory 513 may include one or more memory devices capable of storing data and allowing any storage location to be directly accessed by the microprocessor 507, such as random access memory (RAM), flash memory (e.g., non-volatile flash memory), and the like. The stimulation system 501 may comprise a storage device, such as one or more hard disk drives or redundant arrays of independent disks (RAID), for storing an operating system and other related software, and for storing application software programs, which may be the memory 513 or a different memory. The instructions in memory 513 for the programmable pulse generator 515 can be set and/or modified based on input from the sensors and the analysis of the one or more heart activity properties via the microprocessor 507. The instructions in memory 513 for the programmable pulse generator 515 can also be set and/or modified through inputs from a professional via an input 517 connected through the peripheral bus 509. Examples of such an input include a keyboard and/or a mouse (e.g., in conjunction with a display screen), a touch screen, etc. A wide variety of input/output (I/O) devices may be used with the stimulation system 501. Input devices include, for example, keyboards, mice, trackpads, trackballs, microphones, and drawing tablets. Output devices include, for example, video displays, speakers, and printers. The I/O devices may be controlled by an I/O controller. The I/O controller may control one or more I/O devices. An I/O device may provide storage and/or an installation medium for the stimulation system 501. The stimulation system 501 may provide USB connections to receive handheld USB storage devices. The stimulation system 501 optionally includes a communications port 519 that connects to the peripheral bus 509, where data and/or programming instructions can be received by the microprocessor 507 and/or the memory 513.

Input from the input 517 (e.g., from a professional), the communications port 519, and/or from the one or more heart activity properties via the microprocessor 507 can be used to change (e.g., adjust) the properties of the electrical pulses. The stimulation system 501 optionally includes a power source 521. The power source 521 can be a battery or a power source supplied from an external power supply (e.g., an AC/DC power converter coupled to an AC source). The stimulation system 501 optionally includes a housing 523.

The microprocessor 507 can execute one or more algorithms in order to provide stimulation. The microprocessor 507 can also be controlled by a professional via the input 517 to initiate, terminate, and/or change (e.g., adjust) the properties of the electrical pulses. The microprocessor 507 can execute one or more algorithms to conduct the analysis of the one or more heart activity properties sensed in response to the one or more electrical pulses delivered using the hierarchy of electrode configurations and/or the hierarchy of each property of the one or more electrical pulses, for example to help identify an electrode configuration and/or the property of the one or more electrical pulses delivered to the patient's heart. Such analysis and adjustments can be made using process control logic (e.g., fuzzy logic, negative feedback, etc.) so as to maintain control of the pulse control output generator 511.

The stimulation system 501 may comprise one or more additional components, for example a display device, a cache memory (e.g., in communication with the microprocessor 507), logic circuitry, signal filters, a secondary or backside bus, local buses, local interconnect buses, and the like. The stimulation system 501 may support any suitable installation device, such as a CD-ROM drive, a CD-R/RW drive, a DVD-ROM drive, tape drives of various formats, USB device, hard-drive, communication device to a connect to a server, or any other device suitable for installing software and programs. The stimulation system 501 may include a network interface to interface to a Local Area Network (LAN), Wide Area Network (WAN), or the Internet through a variety of connections including, but not limited to, standard telephone lines, LAN or WAN links, broadband connections, wireless connections (e.g., Bluetooth, WiFi), combinations thereof, and the like. The network interface may comprise a built-in network adapter, network interface card, wireless network adapter, USB network adapter, modem, or any other device suitable for interfacing the stimulation system 501 to any type of network capable of communication and performing the operations described herein. In some embodiments, the stimulation system 501 may comprise or be connected to multiple display devices, which may be of the same or different in type and/or form. As such, any of the I/O devices and/or the I/O controller may comprise any type and/or form of suitable hardware, software, or combination of hardware and software to support, enable, or provide for the connection and use of multiple display devices by the stimulation system 501. The stimulation system can interface with any workstation, desktop computer, laptop or notebook computer, server, handheld computer, mobile telephone, any other computer, or other form of computing or telecommunications device that is capable of communication and that has sufficient processor power and memory capacity to perform the operations described herein and/or to communication with the stimulation system 501. The arrows shown in FIG. 5 generally depict the flow of current and/or information, but current and/or information may also flow in the opposite direction depending on the hardware.

Analysis, determining, adjusting, and the like described herein may be closed loop control or open loop control. For example, in closed loop control, a stimulation system may analyze a heart activity property and adjust an electrical signal property without input from a user. For another example, in open loop control, a stimulation system may analyze a heart activity property and prompt action by a user to adjust an electrical signal property, for example providing suggested adjustments or a number of adjustment options.

In some embodiments, a method of non-therapeutic calibration comprises positioning an electrode in a pulmonary artery of a heart and positioning a sensor in a right ventricle of the heart. The system further comprises delivering, via a stimulation system, a first series of electrical signals to the electrode. The first series comprises a first plurality of electrical signals. Each of the first plurality of electrical signals comprises a plurality of parameters. Each of the first plurality of electrical signals of the first series only differs from one another by a magnitude of a first parameter of the plurality of parameters. The method further comprises, after delivering the first series of electrical signals to the electrode, delivering, via the stimulation system, a second series of electrical signals to the electrode. The second series comprises a second plurality of electrical signals. Each of the second plurality of electrical signals comprises the plurality of parameters. Each of the second plurality of electrical signals of the second series only differs from one another by a magnitude of a second parameter of the plurality of parameters. The second parameter is different than the first parameter. The method further comprises determining, via the sensor, sensor data indicative of one or more non-electrical heart activity properties in response to delivering the first series of electrical signals and the second series of electrical signals. The method further comprises determining a therapeutic neuromodulation signal to be delivered to the pulmonary artery using selected electrical parameters. The selected electrical parameters comprise a selected magnitude of the first parameter and a selected magnitude of the second parameter. The selected magnitudes of the first and second parameters are based at least partially on the sensor data.

In some embodiments, a method of non-therapeutic calibration comprises delivering a first electrical signal of a series of electrical signals to an electrode in a first anatomical location and, after delivering the first electrical signal, delivering a second electrical signal of the series of electrical signals to the electrode. The second electrical signal differs from the first electrical signal by a magnitude of a first parameter of a plurality of parameters. The method further comprises sensing, via a sensor in a second anatomical location different than the first anatomical location, sensor data indicative of one or more non-electrical heart activity properties in response to the delivery of the series of electrical signals, and determining a therapeutic neuromodulation signal to be delivered to the first anatomical location using selected electrical parameters. The selected electrical parameters comprise a selected magnitude of the first parameter. The selected magnitude of the first parameter is based at least partially on the sensor data.

The foregoing description and examples has been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure. Furthermore, all references cited herein are incorporated by reference in their entirety.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Further, the disclosure herein of any particular feature, aspect, method, property, characteristic, quality, attribute, element, or the like in connection with an embodiment can be used in all other embodiments set forth herein. Any methods disclosed herein need not be performed in the order recited. Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some embodiments, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each embodiment. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some embodiments may be performed using the sequence of operations described herein, while other embodiments may be performed following a different sequence of operations.

The various illustrative logical blocks, modules, processes, methods, and algorithms described in connection with the embodiments disclosed herein can be implemented as electronic hardware, computer software, or combinations of both. To clearly illustrate this interchangeability of hardware and software, various illustrative components, blocks, modules, operations, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The blocks, operations, or steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, an optical disc (e.g., CD-ROM or DVD), or any other form of volatile or non-volatile computer-readable storage medium known in the art. A storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "positioning an electrode" include "instructing positioning of an electrode."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±150%, etc.). For example, "about 1 V" includes "1 V." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure.

What is claimed is:

1. A method of facilitating therapeutic neuromodulation of a heart of a patient, the method comprising:
   delivering a first series of electrical signals to an electrode in a first anatomical location,
     the first series comprising a first plurality of electrical signals,
     each of the first plurality of electrical signals comprising a plurality of parameters,
     each of the first plurality of electrical signals of the first series only differing from one another by a magnitude of a first parameter of the plurality of parameters;
   after delivering the first series of electrical signals to the electrode, delivering a second series of electrical signals to the electrode,
     the second series comprising a second plurality of electrical signals,
     each of the second plurality of electrical signals comprising the plurality of parameters,
     each of the second plurality of electrical signals of the second series only differing from one another by a magnitude of a second parameter of the plurality of parameters,
     the second parameter different than the first parameter;
   sensing, via a sensor in a second anatomical location different than the first anatomical location, sensor data indicative of one or more non-electrical heart activity properties in response to delivering the first series of electrical signals and the second series of electrical signals; and
   providing a therapeutic neuromodulation signal to the first anatomical location using selected electrical parameters,
   wherein the selected electrical parameters comprise a selected magnitude of the first parameter and a selected magnitude of the second parameter,
   wherein the selected magnitudes of the first and second parameters are based at least partially on the sensor data, and
   wherein the therapeutic neuromodulation signal increases heart contractility.

2. The method of claim 1, wherein the first parameter comprises current and the second parameter comprises one of frequency and duty cycle.

3. The method of claim 1, further comprising:
   delivering a third series of electrical signals to the electrode,
     the third series comprising a third plurality of electrical signals,
     each of the third plurality of electrical signals comprising the plurality of parameters,
     each of the third plurality of electrical signals of the third series only differing from one another by a magnitude of a third parameter of the plurality of parameters,
     the third parameter different than the first parameter and the second parameter,
   sensing, via the sensor, sensor data indicative of the one or more non-electrical heart activity properties in response to delivering the third series of electrical signals, wherein the selected electrical parameters comprise a selected magnitude of the third parameter, wherein the selected magnitude of the third parameter is based at least partially on the sensor data.

4. The method of claim 3,
wherein delivering the first series of electrical signals to the electrode is via a stimulation system,
wherein delivering the second series of electrical signals to the electrode is via the stimulation system, and
wherein delivering the third series of electrical signals to the electrode is via the stimulation system.

5. The method of claim 1, further comprising determining a desired hierarchy between the first series and the second series.

6. The method of claim 1, wherein the first anatomical location comprises a right pulmonary artery.

7. The method of claim 1, wherein the one or more non-electrical heart activity properties comprises at least one of a pressure property, an acceleration property, an acoustic property, a temperature, and a blood chemistry property.

8. The method of claim 1, wherein sensing the sensor data comprises determining, via a second sensor on a skin surface, sensor data indicative of an electrocardiogram property in response to delivering the first series of electrical signals and the second series of electrical signals.

9. The method of claim 1, wherein the first parameter is one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform.

10. The method of claim 9, wherein the second parameter is a different one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform.

11. The method of claim 1, wherein the second parameter is one of the following: a polarity, a pulsing mode, a pulse width, an amplitude, a frequency, a phase, a voltage, a current, a duration, an inter-pulse interval, a duty cycle, a dwell time, a sequence, a wavelength, or a waveform.

12. The method of claim 1, further comprising:
positioning the electrode in a pulmonary artery of a heart; and
positioning the sensor in a right ventricle of the heart;
wherein delivering the first series of electrical signals to the electrode is via a stimulation system,
wherein delivering the second series of electrical signals to the electrode is via the stimulation system.

13. The method of claim 1, wherein the first anatomical location comprises a pulmonary artery.

14. The method of claim 1, wherein the one or more non-electrical heart activity properties comprises a pressure property.

15. The method of claim 1, wherein the first parameter is one of the following: a pulse width, an amplitude, or a frequency.

16. The method of claim 15, wherein the second parameter is a different one of the following: a pulse width, an amplitude, or a frequency.

17. The method of claim 1, wherein the second parameter is one of the following: a pulse width, an amplitude, or a frequency.

18. The method of claim 1, further comprising:
positioning a catheter including the electrode so the first anatomical position is in a pulmonary artery of a heart; and
positioning the sensor so the second anatomical position is in a location within vasculature of the heart.

19. The method of claim 1, wherein the one or more non-electrical heart activity properties includes an acceleration property.

20. The method of claim 1, wherein the first parameter is one of the following: a pulse width, an amplitude, a frequency, or a duty cycle.

21. The method of claim 20, wherein the second parameter is a different one of the following: a pulse width, an amplitude, a frequency, or a duty cycle.

22. The method of claim 1, wherein the one or more non-electrical heart activity properties includes a temperature.

23. The method of claim 1, wherein the first parameter is one of the following: a pulse width, an amplitude, a frequency, or a waveform.

24. The method of claim 23, wherein the second parameter is a different one of the following: a pulse width, an amplitude, a frequency or a waveform.

25. The method of claim 1, wherein the one or more non-electrical heart activity properties includes a blood chemistry property.

* * * * *